US011370835B2

(12) United States Patent
Brown et al.

(10) Patent No.: US 11,370,835 B2
(45) Date of Patent: Jun. 28, 2022

(54) METHODS FOR PURIFICATION OF SINGLE DOMAIN ANTIGEN BINDING MOLECULES

(71) Applicant: Ablynx N.V., Ghent-Zwijnaarde (BE)

(72) Inventors: Paul R. Brown, Andover, MA (US); Scott Andreas Tobler, South Boston, MA (US); Andrew M. Wood, Newton, PA (US); Austin Wayne Boesch, Somerville, MA (US)

(73) Assignee: Ablynx N.V., Zwijnaarde (BE)

( * ) Notice: Subject to any disclaimer, the term of this patent is extended or adjusted under 35 U.S.C. 154(b) by 715 days.

(21) Appl. No.: 16/142,198

(22) Filed: Sep. 26, 2018

(65) Prior Publication Data

US 2019/0144531 A1    May 16, 2019

Related U.S. Application Data

(62) Division of application No. 12/608,964, filed on Oct. 29, 2009, now Pat. No. 10,118,962.

(60) Provisional application No. 61/109,481, filed on Oct. 29, 2008.

(51) Int. Cl.
*C07K 1/22* (2006.01)
*C07K 16/24* (2006.01)
*C07K 1/18* (2006.01)
*C07K 16/06* (2006.01)
*C07K 16/18* (2006.01)

(52) U.S. Cl.
CPC .............. *C07K 16/241* (2013.01); *C07K 1/18* (2013.01); *C07K 1/22* (2013.01); *C07K 16/065* (2013.01); *C07K 16/18* (2013.01); *C07K 2317/569* (2013.01)

(58) Field of Classification Search
CPC combination set(s) only.
See application file for complete search history.

(56) References Cited

U.S. PATENT DOCUMENTS

| 4,474,893 A | 10/1984 | Reading et al. |
| 4,714,681 A | 12/1987 | Reading et al. |
| 4,816,397 A | 3/1989 | Boss et al. |
| 4,816,567 A | 3/1989 | Cabilly et al. |
| 4,925,648 A | 5/1990 | Hansen et al. |
| 5,223,409 A | 6/1993 | Lander et al. |
| 5,225,539 A | 7/1993 | Winter et al. |
| 5,573,920 A | 11/1996 | Randle et al. |
| 5,585,089 A | 12/1996 | Queen et al. |
| 5,601,819 A | 2/1997 | Wong et al. |
| 5,603,959 A | 2/1997 | Horrobin et al. |
| 5,693,761 A | 12/1997 | Queen et al. |
| 5,693,762 A | 12/1997 | Queen et al. |
| 5,731,168 A | 3/1998 | Carter et al. |
| 5,807,706 A | 9/1998 | Carter et al. |
| 5,821,333 A | 10/1998 | Carter et al. |
| 5,843,440 A | 12/1998 | Pouletty et al. |
| 5,891,996 A | 4/1999 | Mateo de Acosta del Rio et al. |
| 5,976,532 A | 11/1999 | Coller et al. |
| 6,300,064 B1 | 10/2001 | Knappik et al. |
| 6,407,213 B1 | 6/2002 | Carter et al. |
| 6,419,934 B1 | 7/2002 | Tobinick |
| 6,491,934 B1 | 12/2002 | Bekele |
| 6,670,453 B2 | 12/2003 | Frenken et al. |
| 6,759,518 B1 | 7/2004 | Kontermann et al. |
| 7,084,257 B2 | 8/2006 | Deshpande et al. |
| 7,300,655 B2 | 11/2007 | Hansen et al. |
| 7,368,111 B2 | 5/2008 | Thompson et al. |
| 8,071,394 B2 | 12/2011 | Wu et al. |
| 9,393,304 B2 | 7/2016 | Fernandez et al. |
| 9,993,552 B2 | 6/2018 | Fernandez et al. |
| 10,118,962 B2 | 11/2018 | Brown et al. |
| 2002/0001587 A1 | 1/2002 | Erickson et al. |
| 2002/0155537 A1 | 1/2002 | Carter et al. |
| 2002/0054878 A1 | 5/2002 | Lowe et al. |
| 2002/0058033 A1 | 5/2002 | Raisch et al. |
| 2002/0132275 A1 | 9/2002 | Fidler et al. |
| 2002/0165387 A1 | 11/2002 | Kerr Anderson et al. |
| 2003/0020734 A1 | 1/2003 | Yin et al. |
| 2003/0070185 A1 | 4/2003 | Jakobovits et al. |
| 2003/0092892 A1 | 5/2003 | Frenken et al. |
| 2004/0219643 A1 | 11/2004 | Winter et al. |
| 2005/0215470 A1 | 9/2005 | Ng et al. |
| 2005/0266000 A1 | 12/2005 | Bond et al. |
| 2005/0271663 A1 | 12/2005 | Ignatovich et al. |

(Continued)

FOREIGN PATENT DOCUMENTS

| CN | 1299370 A | 6/2001 |
| CN | 101248087 B | 8/2008 |

(Continued)

OTHER PUBLICATIONS

Gagnon et al. "Minibodies and Multimodal chromatography methods: a convergence of challenge and opportunity" Bioprocess Int. Feb. 2010, 8(2): 26-35 (Year: 2010).*
Zwolak et al. "Modulation of protein A binding allows single-step purificaiton of mouse bispecific antibodies taht retain FcRn binding" MABS, 2017, 9(8) pp. 1306-1316 (Year: 2017).*
Akers, Excipient-drug interactions in parenteral formulations. J Pharm Sci. Nov. 2002;91(11):2283-300.
Altschul et al., Basic local alignment search tool. J Mol Biol. Oct. 5, 1990;215(3):403-10.

(Continued)

*Primary Examiner* — Daniel E Kolker
*Assistant Examiner* — James L Rogers
(74) *Attorney, Agent, or Firm* — Wolf, Greenfield & Sacks, P.C.

(57) ABSTRACT

Processes and methods of purifying or separating Single Domain Antigen Binding (SDAB) molecules that include one or more single binding domains (e.g., one or more nanobody molecules), substantially devoid of a complementary antibody domain and an immunoglobulin constant region, using Protein A-based affinity chromatography, are disclosed.

18 Claims, 4 Drawing Sheets
Specification includes a Sequence Listing.

(56) References Cited

U.S. PATENT DOCUMENTS

| | | | |
|---|---|---|---|
| 2006/0034833 A1 | 2/2006 | Silence et al. | |
| 2006/0034845 A1 | 2/2006 | Silence et al. | |
| 2006/0073113 A1 | 4/2006 | Nakamoto et al. | |
| 2006/0106203 A1 | 5/2006 | Winter et al. | |
| 2006/0115470 A1 | 6/2006 | Silence et al. | |
| 2006/0153860 A1 | 7/2006 | Cho et al. | |
| 2006/0228355 A1 | 10/2006 | Silence et al. | |
| 2006/0286066 A1 | 12/2006 | Basran et al. | |
| 2007/0077249 A1 | 4/2007 | Silence et al. | |
| 2007/0178082 A1 | 8/2007 | Silence et al. | |
| 2007/0237769 A1 | 10/2007 | Silence et al. | |
| 2008/0107601 A1 | 5/2008 | Lauwereys et al. | |
| 2008/0260757 A1 | 10/2008 | Holt et al. | |
| 2009/0022721 A1 | 1/2009 | Silence et al. | |
| 2009/0105465 A1 | 4/2009 | Arunakumari et al. | |
| 2009/0238829 A1 | 9/2009 | Silence et al. | |
| 2009/0297535 A1 | 12/2009 | Kolkman et al. | |
| 2009/0306348 A1 | 12/2009 | Goldstein et al. | |
| 2009/0306351 A1* | 12/2009 | Shukla | B01D 15/3809 530/413 |
| 2009/0324512 A1 | 12/2009 | Silence et al. | |
| 2010/0003248 A1 | 1/2010 | Silence et al. | |
| 2010/0003249 A1 | 1/2010 | Silence et al. | |
| 2010/0003253 A1 | 1/2010 | Laeremans et al. | |
| 2010/0021459 A1 | 1/2010 | Silence et al. | |
| 2010/0040613 A1 | 2/2010 | Silence et al. | |
| 2010/0077422 A1 | 3/2010 | Bushinsky | |
| 2010/0137213 A1 | 6/2010 | Fernandez et al. | |
| 2010/0172894 A1 | 7/2010 | Brown et al. | |
| 2010/0297111 A1 | 11/2010 | Beirnaert et al. | |
| 2011/0097302 A1 | 4/2011 | Yuan et al. | |
| 2011/0183861 A1 | 7/2011 | Jonniaux et al. | |
| 2012/0014975 A1 | 1/2012 | Hegen et al. | |
| 2012/0039807 A1* | 2/2012 | Freimoser-Grundschober | A61P 35/00 424/9.1 |
| 2012/0141460 A1* | 6/2012 | Stals | C07K 16/00 424/130.1 |
| 2016/0263220 A1 | 9/2016 | Fernandez et al. | |
| 2018/0353604 A1 | 12/2018 | Fernandez et al. | |

FOREIGN PATENT DOCUMENTS

| | | |
|---|---|---|
| EP | 0 171 496 A2 | 2/1986 |
| EP | 0 173 494 A2 | 3/1986 |
| EP | 0 239 400 A2 | 9/1987 |
| EP | 0 368 684 B1 | 5/1990 |
| EP | 0 584 421 A1 | 3/1994 |
| EP | 0 589 840 A1 | 3/1994 |
| EP | 0 952 218 A2 | 10/1999 |
| EP | 0 954 978 A1 | 11/1999 |
| EP | 1 002 861 A2 | 5/2000 |
| EP | 1 118 669 A2 | 7/2001 |
| EP | 1 816 198 A1 | 8/2007 |
| GB | 2177096 A | 1/1987 |
| GB | 0 115 841.9 | 6/2001 |
| GB | 0 230 202.4 | 12/2002 |
| JP | H09-503384 A | 4/1997 |
| JP | H11-510170 A | 9/1999 |
| JP | 2003-516361 A | 5/2003 |
| JP | 2006-249081 A | 9/2006 |
| JP | 2006-249083 A | 9/2006 |
| JP | 2006-249084 A | 9/2006 |
| JP | 2007-532477 T2 | 11/2007 |
| JP | 2008-533473 A | 8/2008 |
| RU | 2229288 C2 | 5/2004 |
| RU | 2005/134236 A | 6/2006 |
| WO | 1990/002809 A1 | 3/1990 |
| WO | 1990/005144 A1 | 5/1990 |
| WO | 1990/010707 A1 | 9/1990 |
| WO | 1991/000360 A1 | 1/1991 |
| WO | 1991/001743 A1 | 2/1991 |
| WO | 1991/002078 A1 | 2/1991 |
| WO | 1991/017271 A1 | 11/1991 |
| WO | 1992/001047 A1 | 1/1992 |
| WO | WO 1992/001787 A1 | 2/1992 |
| WO | WO 1992/005793 A1 | 4/1992 |
| WO | WO 1992/006193 A1 | 4/1992 |
| WO | WO 1992/008802 A1 | 5/1992 |
| WO | WO 1992/009690 A2 | 6/1992 |
| WO | WO 1992/015679 A1 | 9/1992 |
| WO | WO 1992/016142 A1 | 10/1992 |
| WO | WO 1992/018619 A1 | 10/1992 |
| WO | WO 1992/020791 A1 | 11/1992 |
| WO | WO 1993/001288 A1 | 1/1993 |
| WO | WO 1993/017715 A1 | 9/1993 |
| WO | WO 1994/004678 A1 | 3/1994 |
| WO | WO 1995/010302 A1 | 4/1995 |
| WO | WO 1996/033735 A1 | 10/1996 |
| WO | WO 1996/034096 A1 | 10/1996 |
| WO | WO 1996/034103 A1 | 10/1996 |
| WO | WO 1997/004801 A1 | 2/1997 |
| WO | WO 1997/029131 A1 | 8/1997 |
| WO | WO 1998/052976 A1 | 11/1998 |
| WO | WO 1999/009055 A2 | 2/1999 |
| WO | WO 1999/023221 A2 | 5/1999 |
| WO | WO 1999/057134 A1 | 11/1999 |
| WO | WO 1999/064069 A1 | 12/1999 |
| WO | WO 2000/029004 A1 | 5/2000 |
| WO | WO 2000/034317 A2 | 6/2000 |
| WO | WO 2000/044788 A1 | 8/2000 |
| WO | WO 2000/056772 A2 | 9/2000 |
| WO | WO 2001/041800 A2 | 6/2001 |
| WO | WO 2001/045746 A2 | 6/2001 |
| WO | WO 2001/058956 A2 | 8/2001 |
| WO | WO 2002/015537 A2 | 2/2002 |
| WO | WO 2002/096948 A2 | 5/2002 |
| WO | WO 2002/048193 A2 | 6/2002 |
| WO | WO 2002/051351 A2 | 7/2002 |
| WO | WO 2002/057445 A1 | 7/2002 |
| WO | WO 2002/079781 A1 | 10/2002 |
| WO | WO 2003/014161 A2 | 2/2003 |
| WO | WO 2003/020734 A2 | 3/2003 |
| WO | WO 2003/035694 A2 | 5/2003 |
| WO | WO 2003/080672 | 10/2003 |
| WO | WO-03080655 A1 * 10/2003 ............ C07K 1/22 | |
| WO | WO 2004/001007 A2 | 12/2003 |
| WO | WO 2004/003019 A2 | 1/2004 |
| WO | WO 2004/041862 A2 | 5/2004 |
| WO | WO 2004/041863 A2 | 5/2004 |
| WO | WO 2004/041865 A2 | 5/2004 |
| WO | WO 2004/041867 A1 | 5/2004 |
| WO | WO 2004/060965 A2 | 7/2004 |
| WO | WO 2004/060966 A2 | 7/2004 |
| WO | WO 2004/081026 A2 | 9/2004 |
| WO | WO 2005/044856 A2 | 5/2005 |
| WO | WO 2005/044865 A2 | 5/2005 |
| WO | WO-2005044856 A2 * 5/2005 ............ C07K 1/165 | |
| WO | WO 2006/003388 A2 | 1/2006 |
| WO | WO 2006/059108 A2 | 6/2006 |
| WO | WO 2006/096491 A2 | 9/2006 |
| WO | WO 2006/099308 A2 | 9/2006 |
| WO | WO 2006/122786 A2 | 11/2006 |
| WO | WO 2006/138553 A2 | 12/2006 |
| WO | WO 2006/138737 A2 | 12/2006 |
| WO | WO 2007/014073 A2 | 2/2007 |
| WO | WO-2007019376 A2 * 2/2007 ............ A61K 49/14 | |
| WO | WO 2007/095337 A2 | 8/2007 |
| WO | WO 2007/100535 A2 | 9/2007 |
| WO | WO 2008/071394 A1 | 6/2008 |
| WO | WO 2008/074868 A2 | 6/2008 |
| WO | WO 2008/077945 A2 | 7/2008 |
| WO | WO 2008/086335 A2 | 7/2008 |
| WO | WO 2008/116103 A2 | 9/2008 |
| WO | WO 2009/068627 A2 | 6/2009 |
| WO | WO 2009/133137 A2 | 11/2009 |
| WO | WO 2010/055950 A1 | 5/2010 |
| WO | WO 2010/056550 A1 | 5/2010 |

(56) References Cited

FOREIGN PATENT DOCUMENTS

| | | |
|---|---|---|
| WO | WO 2010/060212 A1 | 6/2010 |
| WO | WO 2010/077422 A2 | 7/2010 |
| WO | WO 2011/026948 A1 | 3/2011 |

OTHER PUBLICATIONS

Altschul et al., Gapped BLAST and PSI-BLAST: a new generation of protein database search programs. Nucleic Acids Res. Sep. 1, 1997;25(17):3389-402.

Arakawa et al., Protein—solvent interactions in pharmaceutical formulations. Pharm Res. Mar. 1991;8(3):285-91.

Arbabi Ghahroudi et al., Selection and identification of single domain antibody fragments from camel heavy-chain antibodies. FEBS Lett. Sep. 15, 1997;414(3):521-6.

Benhar et al., Mutations of two lysine residues in the CDR loops of a recombinant immunotoxin that reduce its sensitivity to chemical derivatization. Bioconjug Chem. Jul.-Aug. 1994;5(4):321-6.

Birch et al., Monoclonal antibodies. Principles and Applications. 1st ed. 1995:237-247.

Blank et al., Expanded bed adsorption in the purification of monoclonal antibodies: a comparison of process alternatives. Bioseparation. 2001;10(1-3):65-71.

Bollag, Ion-exchange chromatography. Methods Mol Biol. 1994;36:11-22.

Bond et al., A structure-based database of antibody variable domain diversity. J Mol Biol. May 6, 2005;348(3):699-709.

Capelle et al., High throughput screening of protein formulation stability: practical considerations. Eur J Pharm Biopharm. Feb. 2007;65(2):131-48. Epub Sep. 29, 2006.

Carpenter et al., Potential inaccurate quantitation and sizing of protein aggregates by size exclusion chromatography: essential need to use orthogonal methods to assure the quality of therapeutic protein products. J Pharm Sci. May 2010;99(5):2200-8. doi: 10.1002/jps.21989.

Cedergren et al., Mutational analysis of the interaction between staphylococcal protein A and human IgG1. Protein Eng. Jun. 1993;6(4):441-8.

Chapman, PEGylated antibodies and antibody fragments for improved therapy: a review. Adv Drug Deliv Rev. Jun. 17, 2002;54(4):531-45.

Chen et al., Influence of histidine on the stability and physical properties of a fully human antibody in aqueous and solid forms. Pharm Res. 2003; 20(12):1952-1960.

Chothia et al., Canonical structures for the hypervariable regions of immunoglobulins. J Mol Biol. Aug. 20, 1987;196(4):901-17.

Chothia et al., Structural repertoire of the human VH segments. J Mol Biol. Oct. 5, 1992;227(3):799-817.

Chuang et al., Pharmaceutical strategies utilizing recombinant human serum albumin. Pharm Res. May 2002;19(5):569-77.

Cleland et al., The development of stable protein formulations: a close look at protein aggregation, deamidation, and oxidation. Crit Rev Ther Drug Carrier Syst. 1993;10(4):307-77.

Colman et al., Effects of amino acid sequence changes on antibody-antigen interactions. Res Immunol. Jan. 1994;145(1):33-6.

Connelly, Fully human domain antibody therapeutics: the best of both worlds. Innovations in Pharmaceutical Technol. 2005;:42-5.

Cook et al., The human immunoglobulin VH repertoire. Immunol Today. May 1995;16(5):237-42.

Cortez-Retamozo et al., Efficient tumor targeting by single-domain antibody fragments of camels. Int J Cancer. Mar. 20, 2002;98(3):456-62.

Daugherty et al., Formulation and delivery issues for monoclonal antibody therapeutics. Adv Drug Deliv Rev. Aug. 7, 2006;58(5-6):686-706. Epub May 22, 2006.

Davies et al., Antibody VH domains as small recognition units. Biotechnology (N Y). May 1995;13(5):475-9.

Decherchi et al., Implicit solvent methods for free energy estimation. Eur J Med Chem. Feb. 16, 2015;91C:27-42. doi: 10.1016/j.ejmech.2014.08.064. Epub Aug. 25, 2014.

Desmyter et al., Antigen specificity and high affinity binding provided by one single loop of a camel single-domain antibody. J Biol Chem. Jul. 13, 2001;276(28):26285-90. Epub May 7, 2001.

D'Haens et al., Endoscopic and histological healing with infliximab anti-tumor necrosis factor antibodies in Crohn's disease: A European multicenter trial. Gastroenterology. May 1999;116(5):1029-34.

Eliasson et al., Differential IgG-binding characteristics of staphylococcal protein A, streptococcal protein G, and a chimeric protein AG. J Immunol. Jan. 15, 1989;142(2):575-81.

Els Conrath et al., Camel single-domain antibodies as modular building units in bispecific and bivalent antibody constructs. J Biol Chem. Mar. 9, 2001;276(10):7346-50. Epub Oct. 25, 2000.

Fahrner et al., Industrial purification of pharmaceutical antibodies: development, operation, and validation of chromatography processes. Biotechnol Genet Eng Rev. 2001;18:301-27.

Frenken et al., Isolation of antigen specific llama VHH antibody fragments and their high level secretion by Saccharomyces cerevisiae. J Biotechnol. Feb. 28, 2000;78(1):11-21.

Fuller et al., Purification of monoclonal antibodies. Curr Protoc Mol Biol. May 2001;Chapter 11:Unit11.11. doi: 10.1002/0471142727.mb1111s37.

Ghose et al., Antibody variable region interactions with Protein A: implications for the development of generic purification processes. Biotechnol Bioeng. Dec. 20, 2005;92(6):665-73.

Gil et al., Strategies to stabilize compact folding and minimize aggregation of antibody-based fragments. Adv Biosci Biotechnol. Apr. 2013;4(4a):73-84.

Gokarn et al., Excipients for Protein Drugs. Ashok et al., (Eds.) 2006. Chapter 17:291-331.

Green et al., Antigen-specific human monoclonal antibodies from mice engineered with human Ig heavy and light chain YACs. Nat Genet. May 1994;7(1):13-21.

Gupta et al., Development of a Multidose Formulation for a Humanized Monoclonal Antibody Using Experimental Design Techniques. AAPSPharm Sci. 2003;5:article 8, p. 1-9.

Hagihara et al., Cellular quality control screening to identify amino acid pairs for substituting the disulfide bonds in immunoglobulin fold domains. J Biol Chem. Jul. 1, 2005;280(26):24752-8. Epub May 3, 2005.

Hagihara et al., Stabilization of an immunoglobulin fold domain by an engineered disulfide bond at the buried hydrophobic region. J Biol Chem. Dec. 14, 2007;282(50):36489-95. Epub Oct. 11, 2007.

Hamers-Casterman et al., Naturally occurring antibodies devoid of light chains. Nature. Jun. 3, 1993;363(6428):446-8.

Harinarayan et al., An exclusion mechanism in ion exchange chromatography. Biotechnol Bioeng. Dec. 5, 2006;95(5):775-87.

Harmsen et al., Llama heavy-chain V regions consist of at least four distinct subfamilies revealing novel sequence features. Mol Immunol. Aug. 2000;37(10):579-90.

Harmsen et al., Passive immunization of guinea pigs with llama single-domain antibody fragments against foot-and-mouth disease. Vet Microbiol. Mar. 10, 2007;120(3-4):193-206. Epub Oct. 28, 2006.

Harmsen et al., Passive immunization of pigs with bispecific llama single-domain antibody fragments against foot-and-mouth disease and porcine immunoglobulin. Vet Microbiol. Nov. 25, 2008;132(1-2):56-64. Epub Apr. 30, 2008.

Harris et al., Effect of pegylation on pharmaceuticals. Nat Rev Drug Discov. Mar. 2003;2(3):214-21.

Hasemann et al., Immunoglobulins: Structure and Function, in William E. Paul, ed. Fundamental Immunology, Second Ed. 1989;209:210-18.

Hawe et al., Forced Degradation of Therapeutic Proteins. J. Pharm Sci. Mar. 2012. 101(3):895-913.

Hober et al., Protein A chromatography for antibody purification. J Chromatogr B Analyt Technol Biomed Life Sci. Mar. 15, 2007;848(1):40-7. Epub Oct. 9, 2006.

Holliger et al., Retargeting serum immunoglobulin with bispecific diabodies. Nat Biotechnol. Jul. 1997;15(7):632-6.

Hoogenboom, Mix and match: building manifold binding sites. Nat Biotechnol. Feb. 1997;15(2):125-6.

(56) References Cited

OTHER PUBLICATIONS

Kostelny et al., Formation of a bispecific antibody by the use of leucine zippers. J Immunol. Mar. 1, 1992; 148(5):1547-53.
Koumenis et al., Modulating pharmacokinetics of an anti-interleukin-8 F(ab')(2) by amine-specific PEGylation with preserved bioactivity. Int J Pharm. Mar. 30, 2000;198(1):83-95.
Kozbor et al., The production of monoclonal antibodies from human lymphocytes. Immunology Today. 1983;4:72-79.
Krinner et al., A highly stable polyethylene glycol-conjugated human single-chain antibody neutralizing granulocyte-macrophage colony stimulating factor at low nanomolar concentration. Protein Eng Des Sel. Oct. 2006;19(10):461-70. Epub Jul. 25, 2006.
Leong et al., Adapting pharmacokinetic properties of a humanized anti-interleukin-8 antibody for therapeutic applications using site-specific pegylation. Cytokine. Nov. 7, 2001;16(3):106-19.
Ljungberg et al., The interaction between different domains of staphylococcal protein A and human polyclonal IgG, IgA, IgM and F(ab')2: separation of affinity from specificity. Mol Immunol. Oct. 1993;30(14):1279-85.
Lloyd et al., Modelling the human immune response: performance of a $10^{11}$ human antibody repertoire against a broad panel of therapeutically relevant antigens. Protein Eng Des Sel. Mar. 2009;22(3):159-68. doi: 10.1093/protein/gzn058. Epub Oct. 29, 2008.
Low et al., Future of antibody purification. J Chromatogr B Analyt Technol Biomed Life Sci. Mar. 15, 2007;848(1):48-63. Epub Nov. 28, 2006.
Lu et al., Effect of PEGylation on the solution conformation of antibody fragments. J Pharm Sci. Jun. 2008;97(6):2062-79.
Macewan, TNF ligands and receptors—a matter of life and death. Br J Pharmacol. Feb. 2002;135(4):855-75.
Mallender et al., Construction, expression, and activity of a bivalent bispecific single-chain antibody. J Biol Chem. Jan. 7, 1994;269(1):199-206.
Martin, Protein Sequence and Structure Analysis of Antibody Variable Domains. In: Antibody Engineering Lab Manual (Ed.: Duebel, Kontermann, Springer-Verlag, Heidelberg). Chapter 3. 2010. 33-51.
Monfardini et al., A branched monomethoxypoly(ethylene glycol) for protein modification. Bioconjugate Chem. Jan. 1, 1995;6(1):62-69.
Morrison et al., Chimeric human antibody molecules: mouse antigen-binding domains with human constant region domains. Proc Natl Acad Sci U S A. Nov. 1984;81(21):6851-5.
Morrison, Transfectomas provide novel chimeric antibodies. Science. Sep. 20, 1985;229(4719):1202-7.
Muyldermans et al., Single domain camel antibodies: current status. J Biotechnol. Jun. 2001;74(4):277-302.
Muyldermans et al., Unique single-domain antigen binding fragments derived from naturally occurring camel heavy-chain antibodies. J Mol Recognit. Mar.-Apr. 1999;12(2):131-40.
Myers et al., Optimal alignments in linear space. CABIOS. 1989;4:11-7.
Needleman et al., A general method applicable to the search for similarities in the amino acid sequence of two proteins. J Mol Biol. Mar. 1970;48(3):443-53.
Nieba et al., Disrupting the hydrophobic patches at the antibody variable/constant domain interface: improved in vivo folding and physical characterization of an engineered scFv fragment. Protein Eng. Apr. 1997;10(4):435-44.
Nilsson et al., A synthetic IgG-binding domain based on staphylococcal protein A. Protein Eng. Feb.-Mar. 1987;1(2):107-13.
Nilsson et al., Affinity fusion strategies for detection, purification, and immobilization of recombinant proteins. Protein Expr Purif. Oct. 1997;11(1):1-16.
O'Donnell et al., A high capacity strong cation exchange resin for the chromatographic purification of monoclonal antibodies and other proteins. PREP. 2007;:1-13.
Oi et al., Chimeric Antibodies. BioTechniques. 1986;4:214.
Olsson et al., Human—human monoclonal antibody-producing hybridomas: technical aspects. Methods Enzymol. 1983;92:3-16.

Paul, Fundamental Immunology, 3rd Edition, under the heading "Fv Structure and Diversity in Three Dimensions." 1993;:292-5.
Pikal, Freeze drying of proteins part II: formulation selection. Biopharm. 1990;3(9):26-30.
Reen et al., Enzyme-linked immunosorbent assay (ELISA). Methods Mol Biol. 1994;32:461-6.
Riechmann et al., Single domain antibodies: comparison of camel VH and camelised human VH domains. J Immunol Methods. Dec. 10, 1999;231(1-2):25-38.
Ring et al., Anaphylactoid reactions to infusions of plasma protein and human serum albumin. Role of aggregated proteins and of stabilizers added during production. Clin Allergy. Jan. 1979;9(1):89-97. Abstract only.
Roben et al., VH3 family antibodies bind domain D of staphylococcal protein A. J Immunol. Jun. 15, 1995;154(12):6437-45.
Roberts et al., Chemistry for peptide and protein PEGylation. Adv Drug Deliv Rev. Jun. 17, 2002;54(4):459-76.
Roguin et al., Monoclonal antibodies inducing conformational change on the antigen molecule. Scandinavian Journal of Immunology. 2003;58:387-94.
Rote et al., Antithrombotic effects of DMP 728, a platelet GPIIb/IIIa receptor antagonist, in a canine model of arterial thrombosis. J Cardiovasc Pharmacol. Apr. 1994;23(4):681-9.
Rudikoff et al., Single amino acid substitution altering antigen-binding specificity. Proc Natl Acad Sci U S A. Mar. 1982;79(6):1979-83.
Rutkoski et al., Human ribonuclease with a pendant poly(ethylene glycol) inhibits tumor growth in mice. Transl Oncol. Aug. 1, 2013;6(4):392-7. Print Aug. 2013. Erratum in: Transl Oncol. 2013;6:5.
Saelman et al., Platelet adhesion to collagen types I through VIII under conditions of stasis and flow is mediated by GPIa/IIa (alpha 2 beta 1-integrin). Blood. Mar. 1, 1994;83(5):1244-50.
Scheurich et al., Quantification and characterization of high-affinity membrane receptors for tumor necrosis factor on human leukemic cell lines. Int J Cancer. Jul. 15, 1986;38(1):127-33.
Shumway et al., XM-ONE[reg] Part 1: The challenges of flow cytometric crossmatching (fcxm) with endothelial/monocyte. American Society for Histocompatibility and Immunogenetics. Poster Session.2009. Abstract 60-P.
Sjödahl et al., Structural studies on the four repetitive Fc-binding regions in protein A from *Staphylococcus aureus*. Eur J Biochem. Sep. 1977;78(2):471-90.
Smith et al., Prolonged in vivo residence times of antibody fragments associated with albumin. Bioconjug Chem. Sep.-Oct. 2001;12(5):750-6.
Smith, Filamentous fusion phage: novel expression vectors that display cloned antigens on the virion surface. Science. Jun. 14, 1985;228(4705):1315-7.
Starovasnik et al., Antibody variable region binding by Staphylococcal protein A: thermodynamic analysis and location of the Fv binding site on E-domain. Protein Sci. Jul. 1999;8(7):1423-31.
Steindl et al., A simple method to quantify staphylococcal protein A in the presence of human or animal IgG in various samples. J Immunol Methods. Feb. 21, 2000;235(1-2):61-9.
Stoscheck, Quantitation of protein. Methods Enzymol. 1990;182:50-68.
Streltsov et al., Structure of a shark IgNAR antibody variable domain and modeling of an early-developmental isotype. Protein Sci. Nov. 2005;14(11):2901-9. Epub Sep. 30, 2005.
Takeda et al., Construction of chimaeric processed immunoglobulin genes containing mouse variable and human constant region sequences. Nature. Apr. 4-10, 1985;314(6010):452-4.
Tamura et al., Structural correlates of an anticarcinoma antibody: identification of specificity-determining residues (SDRs) and development of a minimally immunogenic antibody variant by retention of SDRs only. J Immunol. Feb. 1, 2000;164(3):1432-41.
Tanha et al., Selection by phage display of llama conventional V(H) fragments with heavy chain antibody V(H)H properties. J Immunol Methods. May 1, 2002;263(1-2):97-109.
Tarditi et al., Selective high-performance liquid chromatographic purification of bispecific monoclonal antibodies. J Chromatogr. May 22, 1992;599(1-2):13-20.

(56) References Cited

OTHER PUBLICATIONS

Teng et al., Construction and testing of mouse—human heteromyelomas for human monoclonal antibody production. Proc Natl Acad Sci U S A. Dec. 1983;80(23):7308-12.

Tomlinson et al., The repertoire of human germline VH sequences reveals about fifty groups of VH segments with different hypervariable loops. J Mol Biol. Oct. 5, 1992;227(3):776-98.

Tomlinson et al., The structural repertoire of the human V kappa domain. EMBO J. Sep. 15, 1995;14(18):4628-38.

Tutt et al., Trispecific F(ab')3 derivatives that use cooperative signaling via the TCR/CD3 complex and CD2 to activate and redirect resting cytotoxic T cells. J Immunol. Jul. 1, 1991;147(1):60-9.

Uhleén et al., Complete sequence of the staphylococcal gene encoding protein A. A gene evolved through multiple duplications. J Biol Chem. Feb. 10, 1984;259(3):1695-702.

Valle et al., Infliximab. Expert Opin Pharmacother. Jun. 2001;2(6):1015-25.

Veronese et al., Introduction and overview of peptide and protein pegylation. Adv Drug Deliv Rev. Jun. 17, 2002;54(4):453-6.

Wang, Lyophilization and development of solid protein pharmaceuticals. Int J Pharm. Aug. 10, 2000;203(1-2):1-60.

Ward et al., Binding activities of a repertoire of single immunoglobulin variable domains secreted from *Escherichia coli*. Nature. Oct. 12, 1989;341(6242):544-6.

Worledge et al., Oral administration of avian tumor necrosis factor antibodies effectively treats experimental colitis in rats. Digestive Diseases and Sciences. Dec. 2000;45(12):2298-305.

Yamagishi et al., A new set of atomic radii for accurate estimation of solvation free energy by Poisson-Boltzmann solvent model. J Comput Chem. Nov. 5, 2014;35(29):2132-9. doi: 10.1002/jcc.23728. Epub Sep. 15, 2014.

Yang et al., Tailoring structure-function and pharmacokinetic properties of single-chain Fv proteins by site-specific PEGylation. Protein Eng. Oct. 2003;16(10):761-70.

Yang et al., Tumor necrosis factor alpha blocking peptide loaded PEG-PLGA nanoparticles: preparation and in vitro evaluation. Int J Pharm. Feb. 22, 2007;331(1):123-32. Epub Sep. 17, 2006.

Yarilin, V-domains of immunoglobulins. Antigen-binding sites. Osnovy immunologii, Moskva, Medicina. 1999. 172-174. Russian.

Zaborsky, Immobilized enzymes—miscellaneous methods and general classification. Methods Enzymol. 1976;44:317-32.

Zhang et al., Applications of Modulated Differential Scanning Calorimetry in Polymer Studies. China Acad J. Electronic Publishing House. 2004;341-348.

Zhou et al., Variational Implicit Solvation with Poisson-Boltzmann Theory. J Chem Theory Comput. Apr. 8, 2014;10(4):1454-1467. Epub Feb. 21, 2014.

Zhou, Determining Protein Half-Lives. Methods in Molecular Biology, vol. 284: Signal Transduction Protocols. Edited by: R.C. Dickson. Humana Press Inc., Totowa, NJ. 2004:67-77.

Casset et al., A peptide mimetic of an anti-CD4 monoclonal antibody by rational design. Biochem Biophys Res Commun. Jul. 18, 2003;307(1):198-205. doi: 10.1016/s0006-291x(03)01131-8.

Macallum et al., Antibody-antigen interactions: contact analysis and binding site topography. J Mol Biol. Oct. 11, 1996;262(5):732-45. doi: 10.1006/jmbi.1996.0548.

Skolnick et al., From genes to protein structure and function: novel applications of computational approaches in the genomic era. Trends Biotechnol. Jan. 2000;18(1):34-9. doi: 10.1016/s0167-7799(99)01398-0.

Vajdos et al., Comprehensive functional maps of the antigen-binding site of an anti-ErbB2 antibody obtained with shotgun scanning mutagenesis. J Mol Biol. Jul. 5, 2002;320(2):415-28. doi: 10.1016/S0022-2836(02)00264-4.

Wu et al., Humanization of a murine monoclonal antibody by simultaneous optimization of framework and CDR residues. J Mol Biol. Nov. 19, 1999;294(1):151-62. doi: 10.1006/jmbi.1999.3141.

\* cited by examiner

```
                                            -19 MGWSCIILFLVATATGVHS  -1

1 EVQLVESGGGLVQPGGSLRLSCAASGFTFSDYWMYWVRQAPGKGLEWVSEINTNGLITKY  60

61 PDSVKGRFTISRDNAKNTLYLQMNSLRPEDTAVYYCARSPSGFNRGQGTLVTVSSGGGGS 120

121 GGGSEVQLVESGGGLVQPGNSLRLSCAASGFTFSSFGMSWVRQAPGKGLEWVSSISGSGS 180

181 DTLYADSVKGRFTISRDNAKTTLYLQMNSLRPEDTAVYYCTIGGSLSRSSQGTLVTVSSG 240

241 GGGSGGGSEVQLVESGGGLVQPGGSLRLSCAASGFTFSDYWMYWVRQAPGKGLEWVSEIN 300

301 TNGLITKYPDSVKGRFTISRDNAKNTLYLQMNSLRPEDTAVYYCARSPSGFNRGQGTLVT 360

361 VSS (SEQ ID NO:1)
```

FIGURE 2

```
  1 aqhdeaqqna fyqvlnmpnl nadqrngfiq slkddpsqsa nvlgeaqkln dsqapkadaq
 61 qnkfnkdqqs afyeilnmpn lneeqrngfi qslkddpsqs tnvlgeakkl nesqapkadn
121 nfnkeqqnaf yeilnmpnln eeqrngfiqs lkddpsqsan llaeakklne sqapkadnkf
181 nkeqqnafye ilhlpnlnee qrngfiqslk ddpsqsanll aeakklndaq apkadnkfnk
241 eqqnafyeil hlpnlteeqr ngfiqslkdd psvskeilae akklndaqap keednnkpgk
301 edgnkpgked gnkpgkednk kpgkedgnkp gkednkkpgk edgnkpgked gnkpgkedgn
361 kpgkedgnkp gkedgngvhv vkpgdtvndi akangttadk iaadnkladk nmikpgqelv
421 vdkkqpanha dankaqalpe t (SEQ ID NO:11)
```

FIGURE 4A

```
  1 vdnkfnkeqq nafyeilhlp nlneeqrnaf iqslkddpsq sanllaeakk lndaqapk
    (SEQ ID NO:12)
```

FIGURE 4B

SEQUENCE LISTING

```
<160> NUMBER OF SEQ ID NOS: 12

<210> SEQ ID NO 1
<211> LENGTH: 382
<212> TYPE: PRT
<213> ORGANISM: Artificial Sequence
<220> FEATURE:
<223> OTHER INFORMATION: Synthetic polypeptide
<220> FEATURE:
<221> NAME/KEY: signal
<222> LOCATION: (1)..(19)
<220> FEATURE:
<221> NAME/KEY: mat_peptide
<222> LOCATION: (20)..(382)

<400> SEQUENCE: 1
```

```
Met Gly Trp Ser Cys Ile Ile Leu Phe Leu Val Ala Thr Ala Thr Gly
            -15                 -10                 -5

Val His Ser Glu Val Gln Leu Val Glu Ser Gly Gly Leu Val Gln
        -1  1               5                  10

Pro Gly Gly Ser Leu Arg Leu Ser Cys Ala Ala Ser Gly Phe Thr Phe
        15                  20                  25

Ser Asp Tyr Trp Met Tyr Trp Val Arg Gln Ala Pro Gly Lys Gly Leu
30                  35                  40                  45

Glu Trp Val Ser Glu Ile Asn Thr Asn Gly Leu Ile Thr Lys Tyr Pro
                50                  55                  60

Asp Ser Val Lys Gly Arg Phe Thr Ile Ser Arg Asp Asn Ala Lys Asn
                65                  70                  75

Thr Leu Tyr Leu Gln Met Asn Ser Leu Arg Pro Glu Asp Thr Ala Val
            80                  85                  90

Tyr Tyr Cys Ala Arg Ser Pro Ser Gly Phe Asn Arg Gly Gln Gly Thr
        95                  100                 105

Leu Val Thr Val Ser Ser Gly Gly Gly Gly Ser Gly Gly Gly Ser Glu
110                 115                 120                 125

Val Gln Leu Val Glu Ser Gly Gly Leu Val Gln Pro Gly Asn Ser
                130                 135                 140

Leu Arg Leu Ser Cys Ala Ala Ser Gly Phe Thr Phe Ser Ser Phe Gly
            145                 150                 155

Met Ser Trp Val Arg Gln Ala Pro Gly Lys Gly Leu Glu Trp Val Ser
        160                 165                 170

Ser Ile Ser Gly Ser Gly Ser Asp Thr Leu Tyr Ala Asp Ser Val Lys
        175                 180                 185

Gly Arg Phe Thr Ile Ser Arg Asp Asn Ala Lys Thr Thr Leu Tyr Leu
190                 195                 200                 205

Gln Met Asn Ser Leu Arg Pro Glu Asp Thr Ala Val Tyr Tyr Cys Thr
                210                 215                 220

Ile Gly Gly Ser Leu Ser Arg Ser Ser Gln Gly Thr Leu Val Thr Val
                225                 230                 235

Ser Ser Gly Gly Gly Gly Ser Gly Gly Gly Ser Glu Val Gln Leu Val
        240                 245                 250

Glu Ser Gly Gly Gly Leu Val Gln Pro Gly Gly Ser Leu Arg Leu Ser
        255                 260                 265

Cys Ala Ala Ser Gly Phe Thr Phe Ser Asp Tyr Trp Met Tyr Trp Val
270                 275                 280                 285

Arg Gln Ala Pro Gly Lys Gly Leu Glu Trp Val Ser Glu Ile Asn Thr
                290                 295                 300

Asn Gly Leu Ile Thr Lys Tyr Pro Asp Ser Val Lys Gly Arg Phe Thr
                305                 310                 315

Ile Ser Arg Asp Asn Ala Lys Asn Thr Leu Tyr Leu Gln Met Asn Ser
                320                 325                 330

Leu Arg Pro Glu Asp Thr Ala Val Tyr Tyr Cys Ala Arg Ser Pro Ser
            335                 340                 345

Gly Phe Asn Arg Gly Gln Gly Thr Leu Val Thr Val Ser Ser
350                 355                 360

<210> SEQ ID NO 2
<211> LENGTH: 5
<212> TYPE: PRT
<213> ORGANISM: Artificial Sequence
<220> FEATURE:
```

<223> OTHER INFORMATION: Synthetic peptide

<400> SEQUENCE: 2

Asp Tyr Trp Met Tyr
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic peptide

<400> SEQUENCE: 3

Glu Ile Asn Thr Asn Gly Leu Ile Thr Lys Tyr Pro Asp Ser Val Lys
1               5                   10                  15

Gly

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Ser Pro Ser Gly Phe Asn
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic peptide

<400> SEQUENCE: 5

Ser Phe Gly Met Ser
1               5

<210> SEQ ID NO 6
<211> LENGTH: 17
<212> TYPE: PRT
<213> ORGANISM: Artificial Sequence
<220> FEATURE:
<223> OTHER INFORMATION: Synthetic peptide

<400> SEQUENCE: 6

Ser Ile Ser Gly Ser Gly Ser Asp Thr Leu Tyr Ala Asp Ser Val Lys
1               5                   10                  15

Gly

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7

Gly Gly Ser Leu Ser Arg
1               5

<210> SEQ ID NO 8
<211> LENGTH: 35

```
<212> TYPE: PRT
<213> ORGANISM: Artificial Sequence
<220> FEATURE:
<223> OTHER INFORMATION: Synthetic polypeptide
<220> FEATURE:
<223> OTHER INFORMATION: This sequence may encompass one to seven
      "Gly Gly Gly Gly Ser" repeating units

<400> SEQUENCE: 8

Gly Gly Gly Gly Ser Gly Gly Gly Ser Gly Gly Gly Gly Ser Gly
1               5                   10                  15

Gly Gly Gly Ser Gly Gly Gly Ser Gly Gly Gly Ser Gly Gly
            20                  25                  30

Gly Gly Ser
        35

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Gly Gly Gly Gly Ser Gly Gly Gly Ser
1               5

<210> SEQ ID NO 10
<211> LENGTH: 30
<212> TYPE: PRT
<213> ORGANISM: Artificial Sequence
<220> FEATURE:
<223> OTHER INFORMATION: Synthetic polypeptide
<220> FEATURE:
<223> OTHER INFORMATION: This sequence may encompass four, five or six
      "Gly Gly Gly Gly Ser" repeating units

<400> SEQUENCE: 10

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 11
<211> LENGTH: 441
<212> TYPE: PRT
<213> ORGANISM: Staphylococcal sp.

<400> SEQUENCE: 11

Ala Gln His Asp Glu Ala Gln Gln Asn Ala Phe Tyr Gln Val Leu Asn
1               5                   10                  15

Met Pro Asn Leu Asn Ala Asp Gln Arg Asn Gly Phe Ile Gln Ser Leu
            20                  25                  30

Lys Asp Asp Pro Ser Gln Ser Ala Asn Val Leu Gly Glu Ala Gln Lys
        35                  40                  45

Leu Asn Asp Ser Gln Ala Pro Lys Ala Asp Ala Gln Gln Asn Lys Phe
    50                  55                  60

Asn Lys Asp Gln Gln Ser Ala Phe Tyr Glu Ile Leu Asn Met Pro Asn
65                  70                  75                  80

Leu Asn Glu Glu Gln Arg Asn Gly Phe Ile Gln Ser Leu Lys Asp Asp
                85                  90                  95

Pro Ser Gln Ser Thr Asn Val Leu Gly Glu Ala Lys Lys Leu Asn Glu
            100                 105                 110
```

```
Ser Gln Ala Pro Lys Ala Asp Asn Asn Phe Asn Lys Glu Gln Gln Asn
            115                 120                 125

Ala Phe Tyr Glu Ile Leu Asn Met Pro Asn Leu Asn Glu Glu Gln Arg
        130                 135                 140

Asn Gly Phe Ile Gln Ser Leu Lys Asp Asp Pro Ser Gln Ser Ala Asn
145                 150                 155                 160

Leu Leu Ala Glu Ala Lys Lys Leu Asn Glu Ser Gln Ala Pro Lys Ala
                165                 170                 175

Asp Asn Lys Phe Asn Lys Glu Gln Gln Asn Ala Phe Tyr Glu Ile Leu
            180                 185                 190

His Leu Pro Asn Leu Asn Glu Glu Gln Arg Asn Gly Phe Ile Gln Ser
        195                 200                 205

Leu Lys Asp Asp Pro Ser Gln Ser Ala Asn Leu Leu Ala Glu Ala Lys
    210                 215                 220

Lys Leu Asn Asp Ala Gln Ala Pro Lys Ala Asp Asn Lys Phe Asn Lys
225                 230                 235                 240

Glu Gln Gln Asn Ala Phe Tyr Glu Ile Leu His Leu Pro Asn Leu Thr
                245                 250                 255

Glu Glu Gln Arg Asn Gly Phe Ile Gln Ser Leu Lys Asp Asp Pro Ser
            260                 265                 270

Val Ser Lys Glu Ile Leu Ala Glu Ala Lys Lys Leu Asn Asp Ala Gln
        275                 280                 285

Ala Pro Lys Glu Glu Asp Asn Asn Lys Pro Gly Lys Glu Asp Gly Asn
    290                 295                 300

Lys Pro Gly Lys Glu Asp Gly Asn Lys Pro Gly Lys Glu Asp Asn Lys
305                 310                 315                 320

Lys Pro Gly Lys Glu Asp Gly Asn Lys Pro Gly Lys Glu Asp Asn Lys
                325                 330                 335

Lys Pro Gly Lys Glu Asp Gly Asn Lys Pro Gly Lys Glu Asp Gly Asn
            340                 345                 350

Lys Pro Gly Lys Glu Asp Gly Asn Lys Pro Gly Lys Glu Asp Gly Asn
        355                 360                 365

Lys Pro Gly Lys Glu Asp Gly Asn Gly Val His Val Val Lys Pro Gly
    370                 375                 380

Asp Thr Val Asn Asp Ile Ala Lys Ala Asn Gly Thr Thr Ala Asp Lys
385                 390                 395                 400

Ile Ala Ala Asp Asn Lys Leu Ala Asp Lys Asn Met Ile Lys Pro Gly
                405                 410                 415

Gln Glu Leu Val Val Asp Lys Lys Gln Pro Ala Asn His Ala Asp Ala
            420                 425                 430

Asn Lys Ala Gln Ala Leu Pro Glu Thr
        435                 440

<210> SEQ ID NO 12
<211> LENGTH: 58
<212> TYPE: PRT
<213> ORGANISM: Artificial Sequence
<220> FEATURE:
<223> OTHER INFORMATION: Synthetic polypeptide

<400> SEQUENCE: 12

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30
```

```
Ser Leu Lys Asp Asp Pro Ser Gln Ser Ala Asn Leu Leu Ala Glu Ala
        35                  40                  45

Lys Lys Leu Asn Asp Ala Gln Ala Pro Lys
 50                  55
```

METHODS FOR PURIFICATION OF SINGLE DOMAIN ANTIGEN BINDING MOLECULES

CROSS REFERENCE TO RELATED APPLICATIONS

This application is a divisional of U.S. Ser. No. 12/608,964, filed Oct. 29, 2009, now U.S. Pat. No. 10,118,962, which claims priority to U.S. Ser. No. 61,109,481, filed on Oct. 29, 2008, the entire contents of which are hereby incorporated by reference in their entirety. This application also incorporates by reference the International Application filed with the U.S. Receiving Office on Oct. 29, 2009, entitled "Methods for Purification of Single Domain Antigen Binding Molecules".

SEQUENCE LISTING

The instant application contains a Sequence Listing which has been submitted via EFS-Web and is hereby incorporated by reference in its entirety. Said ASCII copy, created on Oct. 28, 2009, is named 982845_1.txt, and is 10,967 bytes in size.

BACKGROUND

Recombinant proteins such as antibodies typically contain a variety of impurities that need to be removed before the protein product is pharmaceutically acceptable. Some of these impurities may include host cell proteins (HCPs), DNA molecules, variant and/or misfolded forms of the product protein, and high molecular weight aggregates (HMWA). The formation of aggregates is problematic during antibody production as it can adversely affect product safety by causing complement activation or anaphylaxis upon administration. Aggregate formation may also hinder manufacturing processes by causing decreased product yield, peak broadening, and loss of activity. These impurities can have a wide range of retention patterns on different modes of chromatography. Removal of such broad spectrum of impurities is often difficult, typically requiring multiple steps involving different modes of chromatography.

Common protein purification methods are predicated on differences in the size, charge, and solubility between the protein to be purified and the contaminants. Protocols based on these parameters include, but are not limited to, affinity chromatography, ion exchange chromatography, size exclusion chromatography, and hydrophobic interaction chromatography. These chromatographic methods, however, sometimes present technical difficulties in the separation of aggregated or multimeric species of antibodies. Techniques such as ion exchange and hydrophobic interaction chromatography, for example, may induce the formation of aggregates due to an increased protein concentration or the required changes in buffer concentration and/or pH during elusion. Further, in several instances antibodies show differences in isoelectric points that are too small to allow for their separation by ion-exchange chromatography (Tarditi, *J. Immunol. Methods* 599:13-20 (1992)). Size exclusion chromatography tends to be cumbersome and results in the significant dilution of the product, which is a hindrance in large-scale, efficiency-based manufacturing processes. Leakage of ligands from affinity chromatography columns can also occur, which results in undesirable contamination of the eluted product (Steindl, *J. Immunol. Methods* 235: 61-69 (2000)).

While several different modalities of chromatography can be employed during the purification of recombinant proteins, the need still exists to develop purification processes that reduce the number of chromatography steps used and that do not destroy, or significantly reduce, the biological activity of the recombinant protein.

SUMMARY

The present invention is based, in part, on the discovery that single domain antigen binding (SDAB) molecules interact with, e.g., bind to, Protein A or a functional variant thereof, thereby enabling the use of Protein A-based affinity chromatography in the purification of the SDAB molecules. In other embodiments, the SDAB molecules can be purified using other chromatographic techniques, such as ion (e.g., cation) exchange chromatography. The SDAB molecule can include one or more single antigen binding domains that interact with, e.g., bind to, one or more target proteins (e.g., tumor necrosis factor and/or human serum albumin). In certain embodiments, the SDAB molecule is a single chain polypeptide comprised of one or more nanobody molecules, being substantially devoid of a complementary antibody domain and/or an immunoglobulin constant region. Thus, the present invention relates to processes and methods of purifying or separating SDAB molecules that include one or more single binding domains (e.g., one or more nanobody molecules), using chromatographic techniques such as Protein A-based affinity chromatography and ion (e.g., cation) exchange chromatography, individually or in combination. [Note: Nanobody™ and Nanobodies™ are registered trademarks of Ablynx N.V.]

Accordingly, in one aspect, the invention features a method, or process, of separating or purifying an SDAB molecule (e.g., one or more nanobody molecules) from a mixture containing the SDAB molecule and one or more contaminants (also referred to herein as an "SDAB molecule preparation"). The method or process includes: contacting the mixture with a Protein A-based support or an ion (e.g., cation) exchange (CEX) support, under conditions that allow the SDAB molecule to bind or absorb to the support; removing one or more contaminants, e.g., by washing the bound support under conditions where the SDAB molecule remains bound to the support (e.g., washing the bound support with at least one Protein A or CEX washing buffer); and selectively eluting the SDAB molecule from the support, e.g., by eluting the adsorbed SDAB molecule with at least one Protein A or CEX elution buffer.

In one embodiment, the method of separating or purifying the SDAB molecule includes contacting the mixture of the SDAB molecule and one or more contaminants with a cation exchange support.

In other embodiments, the method of separating or purifying the SDAB molecule includes contacting the mixture of the SDAB molecule and one or more contaminants with a Protein A-based resin.

The method or process can be used alone, or in combination with, at least one other purification method, including, but not limited to, one or more of: hydroxyapatite, affinity chromatography, size exclusion chromatography, hydrophobic interaction chromatography, metal affinity chromatography, diafiltration, ultrafiltration, viral inactivation (e.g., using low pH) and/or viral removal filtration. For example, the method or process can be used in combination with one or more of hydroxyapatite chromatography, ultrafiltration, viral inactivation (e.g., using low pH) and/or viral removal filtration. In embodiments where a Protein A-support is used, the method or process can further include ion (e.g., cation or anion) exchange chromatography.

In embodiments, the method or process further includes contacting the mixture with a hydroxyapatite resin and selectively eluting the SDAB molecule from the hydroxyapatite resin. In other embodiments where a Protein A-support is used, the method or process further includes contacting the mixture with a cation exchange (CEX) column, and selectively eluting the SDAB molecule from the column.

Embodiments of the aforesaid methods and processes may include one or more of the following features:

In one embodiment, the SDAB molecule separated or purified by the method or process of the invention is a recombinant protein produced as a product of a cell culture, e.g., a host cell (e.g., a mammalian, e.g., a Chinese Hamster Ovary (CHO), cell) in a mixture that includes the SDAB molecule and cell culture contaminants. The cell culture can be a small or a large scale culture.

In other embodiments, the contaminants in the mixture separated or purified by the method or process of the invention include one or more of high molecular weight protein aggregates, host cell proteins, DNA, and/or Protein A (e.g., leached protein A). In embodiments, the SDAB molecule is purified to at least 85%, 90%, 95%, 96%, 97%, 98%, 99% or higher purity.

In another embodiment, the Protein A-based support used in the method or process of the invention includes a support, e.g., a resin, of immobilized Protein A (e.g., recombinant or isolated Protein A), or a functional variant thereof. In one embodiment, the immobilized Protein A is full length Staphylococcal Protein A (SpA) composed of five domains of about 50-60 amino acid residues known as E, D, A, B and C domains in order from the N-terminus. For example, the Protein A includes the amino acid sequence of SpA (SEQ ID NO:11) shown in FIG. 4A, or an amino acid sequence substantially identical thereto (e.g., an amino acid sequence at least 85%, 90%, 95% or more identical to the amino acid sequence of SEQ ID NO:11 shown in FIG. 4A). In other embodiments, the immobilized Protein A is a functional variant of SpA that includes at least one domain chosen from E, D, A, B and/or C, or a modified form thereof. For example, the functional variant of SpA can include at least domain B of SpA, or a variant of domain B, having one or more substituted asparagine residues, also referred to herein as domain Z. In one embodiment, the functional variant of SpA includes the amino acid sequence of SEQ ID NO:12 shown in FIG. 4B, or an amino acid sequence substantially identical thereto (e.g., an amino acid sequence at least 85%, 90%, 95% or more identical to the amino acid sequence of SEQ ID NO:12 shown in FIG. 4B). Other permutations of functional variants of Protein A can be used comprising domain B, or a variant domain B, and one or more of: domains A and/or C; domains E, A and/or C; or domains E, D, A and/or C. Any combination of E, D, A, B and/or C, or a functional variant thereof, can be used as long as the combination is capable of binding to the SDAB molecule. Exemplary Protein A support resins that can be used include MabSELECT™ columns, MabSELECT™ SuRe columns, MabSELECT™ Xtra (GE Healthcare Products), and ProSep™ Va Ultra Plus (Millipore Corporation, Billerica Mass.).

In one embodiment where a Protein A-based support is used in the method or process of the invention, the mixture of SDAB molecules and contaminants are contacted with, e.g., loaded onto, the Protein A-based support under conditions that allow the SDAB molecule to bind or absorb to the Protein A-based support. In certain embodiments, a Protein A loading buffer is used that includes a conditioned medium. The Protein-A column can be equilibrated using a Protein A equilibration solution that includes about 10 to about 250 mM NaCl and about 10 to about 100 mM Tris at pH ranging from about 6 to 8; about 50 to about 200 mM NaCl and about 20 to about 75 mM Tris at pH ranging from about 6.5 to 7.5; about 100 to about 175 mM NaCl and about 40 to about 60 mM Tris at pH ranging from about 7 to 7.5; about 125 to about 160 mM NaCl and about 45 to about 55 mM Tris at pH ranging from about 7 to 7.5; about 50 to about 150 mM NaCl and about 50 mM Tris at pH ranging from about 7.5; or about 150 mM NaCl and about 50 mM Tris at pH ranging from about 6.5, 7.0, 7.5, or 8.0.

In yet another embodiment where a Protein A-based support is used in the method or process of the invention, one or more contaminants of the mixture are removed, e.g., by washing the bound support under conditions where the SDAB molecule remains bound to the support (e.g., washing the bound support with at least one Protein A washing buffer). In certain embodiments, the Protein A washing buffer includes includes about 10 to about 250 mM NaCl and about 10 to about 100 mM Tris at pH ranging from about 6 to 8; about 50 to about 200 mM NaCl and about 20 to about 75 mM Tris at pH ranging from about 6.5 to 7.5; about 100 to about 175 mM NaCl and about 40 to about 60 mM Tris at pH ranging from about 7 to 7.5; about 125 to about 160 mM NaCl and about 45 to about 55 mM Tris at pH ranging from about 7 to 7.5; about 50 to about 150 mM NaCl and about 50 mM Tris at pH ranging from about 7.5; or about 150 mM NaCl and about 50 mM Tris at pH ranging from about 6.5, 7.0, 7.5, or 8.0. In some embodiments, the washing buffer includes 50 mM NaCl and 50 mM Tris at pH 7.5. In some embodiments, the washing buffer includes 10 mM, 25 mM, 50 mM, 75 mM, 100 mM, 150 mM, 200 mM, 250 mM, 300 mM, 350 mM, 400 mM, 450 mM, or 500 mM NaCl. In some embodiments, the washing buffer includes 10 mM, 25 mM, 50 mM, 75 mM, 100 mM, 150 mM, 200 mM, 250 mM, 300 mM, 350 mM, 400 mM, 450 mM, or 500 mM $CaCl_2$. In some embodiments, the washing buffer includes 10 mM, 25 mM, 50 mM, 75 mM, 100 mM, 150 mM, 200 mM, 250 mM, 300 mM, 350 mM, 400 mM, 450 mM, or 500 mM Tris. In some embodiments, the washing buffer includes 10 mM, 25 mM, 50 mM, 75 mM, 100 mM, 150 mM, 200 mM, 250 mM, 300 mM, 350 mM, 400 mM, 450 mM, or 500 mM Citrate. In some embodiments, the washing buffer includes 10 mM, 25 mM, 50 mM, 75 mM, 100 mM, 150 mM, 200 mM, 250 mM, 300 mM, 350 mM, 400 mM, 450 mM, or 500 mM HEPES. In some embodiments, the washing buffer is at pH 6.0, 6.5, 7.0, 7.5, 8.0, 8.5 or 9.0.

In yet another embodiment where a Protein A-based support is used in the method or process of the invention, the SDAB molecule is selectively eluted from the support, e.g., by eluting the adsorbed SDAB molecule with at least one Protein A elution buffer. In some embodiments, the elution buffer includes about 5 to about 50 mM NaCl and about 5 mM to about 100 mM glycine at pH 4.0 or less. In some embodiments, the elution buffer includes about 10 mM, about 25 mM, about 50 mM, about 75 mM, about 100 mM, about 150 mM, about 200 mM, about 250 mM, about 300 mM, about 350 mM, about 400 mM, about 450 mM, or about 500 mM NaCl; about 10 mM, about 25 mM, about 50 mM, about 75 mM, about 100 mM, about 150 mM, about 200 mM, or about 250 mM glycine. In some embodiments, the elution buffer is at pH 2.0, 2.5, 3.0, 3.5, or 4.0. In certain embodiments, the Protein A eluting buffer includes about 10 mM NaCl and about 50 mM glycine at about pH 3.0.

In one embodiment, ceramic hydroxyapatite chromatography is used in combination with Protein A chromatography in the method or process of the invention. The ceramic hydroxyapatite chromatography can be used prior to, or more frequently after, the Protein-A based chromatography. In such embodiments, the method includes contacting the mixture of the SDAB molecule (e.g., the mixture after separation or purification with Protein A chromatography) with a hydroxyapatite resin and selectively eluting the SDAB molecule from the resin. Alternatively the mixture may be pre-treated with an equilibration buffer and then allowed to flow through a hydroxyapatite resin. Either of these methods may also be used in combination to purify the mixtures. In one embodiment, the elution and load buffers include about 1 to about 20 mM sodium phosphate and from about 0.2 to about 2.5 M sodium chloride, wherein the elution and load buffers have a pH from about 6.4 to about 7.6. In other embodiments, the equilibration buffer and wash buffer include about 1 to about 20 mM sodium phosphate, from about 0.01 to about 2.0 M sodium chloride, from about 0 to about 200 mM arginine, and from about 0 to about 200 mM HEPES, wherein the equilibration and wash buffers have a pH from about 6.2 to 8.0. In embodiments, the resulting purified SDAB molecule contains less than 10%, 9%, 8%, 7%, 6%, 5%, 4%, 3%, 2%, 1% or less high molecular weight aggregates.

In other embodiments, the ion exchange chromatography is used in combination with one or both of Protein A chromatography and/or hydroxyapatite chromatography as described herein. An exemplary method or process where the Protein A chromatography is carried out before the ion exchange chromatography includes: contacting the mixture containing the SDAB molecule and one or more contaminants with a Protein A support, allowing the SDAB molecule to adsorb to the support, washing the support and adsorbed SDAB molecule with at least one Protein A washing buffer, eluting the adsorbed SDAB molecule with at least one Protein A elusion buffer, thereby collecting an SDAB molecule preparation. The method or process can further include contacting the SDAB molecule preparation with an ion exchange support, allowing the SDAB molecule to flow through the support, washing the support with at least one ion exchange washing buffer, thereby collecting the ion exchange flow-through. In certain embodiments, the method or process further includes contacting the ion exchange flow-through with a hydroxyapatite resin, allowing the flow-through to adsorb to the resin, washing the resin with at least one hydroxyapatite washing buffer, and eluting purified SDAB molecule from the resin with at least one hydroxyapatite elusion buffer.

In other embodiments, ion (e.g., cation) exchange chromatography (CEX) is used alone, or in combination with another resin, e.g., one or both of Protein A chromatography and/or ceramic hydroxyapatite chromatography. The method or process includes contacting the mixture containing the SDAB molecule and one or more contaminants with an ion exchange support, allowing the SDAB molecule to flow through the support, washing the support with at least one ion (e.g., cation) exchange washing buffer. In one embodiment, cation exchange support is chosen from: Capto™ S (GE Heathcare), Fractogel® SO3-(M) (EMD Chemicals), Toyopearl® Gigacap S-650M (Tosoh Bioscience) or Poros® HS 50 (Applied Biosystems). In one embodiment, the CEX resin shows a capacity of at least about 10 g/L, 20 g/L, 30 g/L, 40 g/L, 50 g/L, or 60 g/L. In other embodiments, the conductivity of the condition media (CM) used to load the column is between about 15 and 5 mS/cm, 14 and 6 mS/cm, 13 and 8 mS/cm, 12 and 9 mS/cm, or 11 to 10 mS/cm, or about 7 mS/cm, 8 mS/cm, 9 mS/cm, 10 mS/cm, 11 mS/cm, 12 mS/cm, or 13 mS/cm. In other embodiments, the pH of the loading conditions is adjusted to less than about 6, 5.5, 5, 4.5, 4.4, 4.3, 4.2, 4.1, 4, 3.9, 3.8, or 3.7. In embodiments, the elution buffer is about 100 mM sodium chloride or less, about 90 mM sodium chloride or less, about 80 mM sodium chloride or less, about 70 mM sodium chloride or less, about 60 mM sodium chloride or less, about 50 mM sodium chloride or less, about 40 mM sodium chloride or less, or about 30 mM sodium chloride or less, 20 mM sodium chloride or less, about 10 mM sodium chloride or less, about 5 mM sodium chloride or less, about 1 mM sodium chloride or less, and has a pH of about 4 to 8, about 5 to 7.5, about 5.5 to 7.2, about 6 to 7.1, or about 6.5 to 7, or about 5, 5, 5, 6, 6, 5, or 7. In other embodiments, the CEX column could also be eluted using the downstream cHA equilibration buffer.

In certain embodiments, the cation exchange chromatography is the only chromatographic method used in the SDAB purification. In other embodiments, cation exchange chromatography is used in combination with other chromatographic methods (e.g., hydroxyapatite chromatography). An exemplary method or process where the cation exchange chromatography is carried out includes: contacting the mixture containing the SDAB molecule and one or more contaminants with a cation exchange support under conditions that reduce the conductivity of the loading buffer or conditioned medium (e.g., under conditions about 15 and 5 mS/cm, 14 and 6 mS/cm, 13 and 8 mS/cm, 12 and 9 mS/cm, or 11 to 10 mS/cm, or about 7 mS/cm, 8 mS/cm, 9 mS/cm, 10 mS/cm, 11 mS/cm, 12 mS/cm, or 13 mS/cm), allowing the SDAB molecule to adsorb to the support, washing the support and adsorbed SDAB molecule with at least one cation exchange washing buffer, eluting the adsorbed SDAB molecule with at least one elusion buffer, thereby collecting an SDAB molecule preparation. The method or process can further include contacting the SDAB molecule preparation with another support or resin, for example, the method or process can further include contacting the ion exchange flow-through with a hydroxyapatite resin, allowing the flow-through to adsorb to the resin, washing the resin with at least one hydroxyapatite washing buffer, and eluting purified SDAB molecule from the resin with at least one hydroxyapatite elusion buffer.

In other embodiments, the method or process further includes concentrating the eluted SDAB molecule, e.g., by performing an ultrafiltration/diafiltration step, to a preset target volume. The concentration step can also be used to exchange the buffer of the eluted SDAB molecule. For example, the concentrated, eluted SDAB molecule can be filtered, e.g., diafiltered, in the presence of a Histidine buffer or a Tris buffer. In embodiments where the Histidine buffer is used, the buffer is at a concentration of at least about 5 to 30 mM, about 7.5 to 28 mM, about 10 to 20 mM, about 12 to 15 mM, or about 10 mM, about 11 mM, about 12 mM, about 13 mM, about 14 mM, about 15 mM, about 20 mM, about 25 mM, about 28 mM at a pH of about 7, about 6, about 5, about 4, about 3, or in the range of about 4 to 6.5, about 5 to 6, about 5.9, about 5.8, about 5.7, about 5.6, or about 5.5. In embodiments, a small volume of concentrated formulation buffer is added to the eluted, concentrated SDAB molecule (e.g., at least 2, 5, 8, 9, 10, 11, 12, 13, 14, 15, 16, 17, 18, 20% v/v of the concentrated formulation buffer. In embodiments, the concentrated formulation buffer is about 10 to 50 mM Histidine (e.g., about 20 mM, about 30 mM Histidine, about 10 to 60% sugar (e.g., sucrose, sorbitol or trehalose), e.g., about 50% sucrose, and a surfactant (e.g., polysorbate 80) at about 0.001 to about 0.1%, e.g., about 0.06%). Exemplary formulations for the SDAB molecules are described in U.S. Ser. No. 12/608,553, filed on Oct. 29, 2008 in the name of Wyeth, the contents of which are incorporated by reference herein.

In embodiments, the SDAB molecule is concentrated to at least about 20 g/L, 30 g/L, 40 g/L, 80 g/L, 90 g/L g/L, 100 g/L, 150 g/L, 200 g/L, 210 g/L, 220 g/L, 230 g/L, 240 g/L, 250 g/L, 260 g/L, 270 g/L, 280 g/L, 290 g/L, 300 g/L, 310 g/L, 320 g/L, 330 g/L, 340 g/L, 350 g/L or higher.

In certain embodiments, the method or process includes: evaluating (e.g., detecting, quantifying and/or monitoring) at least one parameter of the purity, activity, toxicity, pharmacokinetics and/or pharmacodynamics of the SDAB molecule; (optionally) comparing the at least one parameter with a reference value, to thereby evaluate or select the SDAB molecule. The comparison can include determining if the at least one parameter has a pre-selected relationship with the reference value, e.g., determining if it falls within a range of the reference value (either inclusive or exclusive of the endpoints of the range); is equal to or greater than the reference value. In certain embodiments, if the at least one parameter meets a pre-selected relationship, e.g., falls within the reference value, the SDAB molecule is selected. In other embodiments, the assays, methods, or an indication of whether the pre-selected relationship between the at least one parameter and a reference value is met, is recorded or memorialized, e.g., in a computer readable medium. Such methods, assays or indications of meeting pre-selected relationship can be listed on the product insert, a compendium (e.g., the U.S. Pharmacopeia), or any other materials, e.g., labeling that may be distributed, e.g., for commercial use, or for submission to a U.S. or foreign regulatory agency.

In one embodiment, the method or process further includes comparing the value determined with a reference value, to thereby analyze the manufacturing process.

In one embodiment, the method further includes maintaining the manufacturing process based, at least in part, upon the analysis. In one embodiment, the method further includes altering the manufacturing process based upon the analysis.

In another embodiment the method includes evaluating a process, e.g., manufacturing process, of the SDAB molecule, e.g., a TNF nanobody molecule, made by a selected process, that includes making a determination about the process based upon a method or analysis described herein. In one embodiment, the method further includes maintaining or altering the manufacturing process based, at least in part, upon the method or analysis. Thus, in another embodiment the party making the evaluation does not practice the method or analysis described herein but merely relies on results which are obtained by a method or analysis described herein.

In another embodiment the method includes comparing two or more preparations in a method of monitoring or controlling batch-to-batch variation or to compare a preparation to a reference standard.

In yet another embodiment, the method can further include making a decision, e.g., to classify, select, accept or discard, release or withhold, process into a drug product, ship, move to a different location, formulate, label, package, release into commerce, sell or offer for sale the preparation, based, at least in part, upon the determination.

In another aspect, the invention features a method of complying with a regulatory requirement, e.g., a post approval requirement of a regulatory agency, e.g., the FDA. The method includes providing an evaluation of a parameter of SDAB molecule, as described herein. The post approval requirement can include a measure of one more of the above parameters. The method also includes, optionally, determining whether the observed solution parameter meets a preselected criteria or if the parameter is in a preselected range; optionally, memorializing the value or result of the analysis, or communicating with the agency, e.g., by transmitting the value or result to the regulatory agency.

In another aspect, the invention features a method of one or more of: providing a report to a report-receiving entity, evaluating a sample of an SDAB molecule, e.g., a TNF nanobody molecule, for compliance with a reference standard, e.g., an FDA requirement, seeking indication from another party that a preparation of the SDAB molecule meets some predefined requirement, or submitting information about a preparation of an SDAB molecule to another party. Exemplary receiving entities or other parties include a government, e.g., the U.S. federal government, e.g., a government agency, e.g., the FDA. The method includes one or more (or all) of the following steps for making and/or testing the SDAB molecule in a first country, e.g., the U.S.; sending at least an aliquot of the sample outside the first country, e.g., sending it outside the United States, to a second country; preparing, or receiving, a report which includes data about the structure of the preparation of the SDAB molecule, e.g., data related to a structure and/or chain described herein, e.g., data generated by one or more of the methods described herein; and providing said report to a report recipient entity.

The SDAB molecule, e.g., the nanobody molecule (e.g., the TNF-binding nanobody molecule) separated or purified by the method or process of the invention can include one or more single binding domains (e.g., one or more nanobodies). For example, the nanobody molecule can comprise, or consist of, a polypeptide, e.g., a single chain polypeptide, comprising at least one immunoglobulin variable domain (including one, two or three complementarity determining regions (CDRs)). Examples of SDAB molecules include molecules naturally devoid of light chains (e.g., VHH, nanobodies, or camelid derived antibodies). Such SDAB molecules can be derived or obtained from camelids such as camel, llama, dromedary, alpaca and guanaco. In other embodiments, the SDAB molecule may include single domain molecules including, but not limited to, other naturally-occurring single domain molecules, such as shark single domain polypeptides (IgNAR); and single domain scaffolds (e.g., fibronectin scaffolds). Single domain molecules may be derived from shark.

In one embodiment, the SDAB molecule separated or purified by the method or process of the invention is a single chain polypeptide comprised of one or more single domain molecules. In embodiments, the nanobody molecule is monovalent or multivalent (e.g., bivalent, trivalent, or tetravalent). In other embodiments, the nanobody molecule is monospecific or multispecific (e.g., bispecific, trispecific or tetraspecific). The SDAB molecule may comprise one or more single domain molecules that are recombinant, CDR-grafted, humanized, camelized, de-immunized, and/or in vitro generated (e.g., selected by phage display). For example, the SDAB molecule can be a single chain fusion polypeptide comprising one or more single domain molecules that binds to one or more target antigens. Typically, the target antigen is a mammalian, e.g., a human protein. In certain embodiments, the SDAB molecule binds to a serum protein, e.g., a human serum proteins chosen from one or more of serum albumin (human serum albumin (HSA)), fibrin, fibrinogen, or transferrin.

In one exemplary embodiment, the SDAB molecule separated or purified by the method or process of the invention is a trivalent, bispecific molecule composed of a single chain polypeptide fusion of two single domain molecules (e.g., two camelid variable regions) that bind to a target antigen, e.g., tumor necrosis factor α (TNF α), and one single domain molecule (e.g., a camelid variable region) that binds to a serum protein, e.g., HSA. The single domain molecules of the SDAB molecule can be arranged in the following order from N- to C-terminus: TNFα-binding single domain molecule—HAS-binding single domain molecule—TNFα-binding single domain molecule. It will be appreciated that any order or combination of single domain molecules against one or more targets can be formulated as described herein.

In one embodiment, the SDAB molecule separated or purified by the method or process of the invention is referred to herein as "ATN-103," comprises, or consists of, the amino acid sequence of SEQ ID NO:1 shown in FIG. 2, or an amino acid sequence substantially identical thereto (e.g., an amino acid sequence at least 85%, 90%, 95% or more identical to the amino acid sequence of SEQ ID NO:1 shown in FIG. 2). Examples of additional trivalent, bispecific nanobody molecules that can be formulated as described herein include TNF24, TNF25, TNF26, TNF27, TNF28, TNF60 and TNF62 disclosed in Table 29 of WO 2006/122786.

In certain embodiments, at least one of the single domain molecule of the SDAB molecule separated or purified by the method or process of the invention binds to TNFα includes one, two, or three CDRs having the amino sequence: DYWMY (CDR1), EINTNGLITKYPDSVKG (CDR2) and/or SPSGFN (CDR3), or having a CDR that differs by fewer than 3, 2 or 1 amino acid substitutions (e.g., conservative substitutions) from one of said CDRs. In other embodiments, the single domain molecule comprises a variable region having the amino acid sequence from about amino acids 1 to 115 of SEQ ID NO:1 shown in FIG. 2, or an amino acid sequence substantially identical thereto (e.g., an amino acid sequence at least 85%, 90%, 95% or more identical to the amino acid sequence of SEQ ID NO:1 shown in FIG. 2). In embodiments, the TNFα-binding single domain molecule has one or more biological activities of the TNFα-binding single domain antibody molecule of SEQ ID NO:1 shown in FIG. 2. For example, the TNFα-binding single domain molecule binds to the same or a similar epitope as the epitope recognized by the TNFα-binding single domain molecule of SEQ ID NO:1 shown in FIG. 2 (e.g., binds to TNFα in its trimeric form; binds to the TNFα site contacting the TNF receptor; binds to an epitope in the TNFα trimer comprising Gln at position 88 and Lys at position 90 on the first TNF monomer (monomer A), and Glu at position 146 on the second TNF monomer (monomer B), or an epitope as disclosed in WO 06/122786). In other embodiment, the TNFα-binding single domain molecule has an activity (e.g., binding affinity, dissociation constant, binding specificity, TNF-inhibitory activity) similar to any of the TNFα-binding single domain molecule disclosed in WO 06/122786.

In other embodiments, the TNFα-binding nanobody molecule comprises one or more of the nanobodies disclosed in WO 2006/122786. For example, the TNFα-binding nanobody molecule can be a monovalent, bivalent, trivalent TNFα-binding nanobody molecule disclosed in WO 2006/122786. Exemplary TNFα-binding nanobodies include, but are not limited to, TNF1, TNF2, TNF3, humanized forms thereof (e.g., TNF29, TNF30, TNF31, TNF32, TNF33). Additional examples of monovalent TNFα-binding nanobodies are disclosed in Table 8 of WO 2006/122786. Exemplary bivalent TNFα-binding nanobody molecules include, but are not limited to, TNF55 and TNF56, which comprise two TNF30 nanobodies linked via a peptide linker to form a single fusion polypeptide (disclosed in WO 2006/122786). Additional examples of bivalent TNFα-binding nanobody molecules are disclosed in Table 19 of WO 2006/122786 as TNF4, TNF5, TNF6, TNF7, TNF8).

In other embodiments, at least one of the single domain molecule of the SDAB molecule separated or purified by the method or process of the invention binds to HSA includes one, two, or three CDRs having the amino sequence: SFGMS (CDR1), SISGSGSDTLYADSVKG (CDR2) and/or GGSLSR (CDR3), or having a CDR that differs by fewer than 3, 2 or 1 amino acid substitutions (e.g., conservative substitutions) from one of said CDRs. In other embodiments, the single domain molecule comprises a variable region having the amino acid sequence from about amino acids 125 to 239 of SEQ ID NO:1 shown in FIG. 2, or an amino acid sequence substantially identical thereto (e.g., an amino acid sequence at least 85%, 90%, 95% or more identical to the amino acid sequence of SEQ ID NO:1 shown in FIG. 2). In embodiments, the HSA-binding single domain molecule has one or more biological activities of the HSA-binding single domain molecule of SEQ ID NO:1 shown in FIG. 2. For example, the HSA-binding single domain molecule binds to the same or a similar epitope as the epitope recognized by the HSA-binding single domain molecule of SEQ ID NO:1 shown in FIG. 2. In other embodiment, the HSA-binding single domain molecule has an activity (e.g., binding affinity, dissociation constant, binding specificity) similar to any of the HSA-binding single domain molecule disclosed in WO 06/122786.

In other embodiments, the HSA-binding SDAB molecule comprises one or more of the nanobodies disclosed in WO 2006/122786. For example, the HSA-binding SDAB molecule can be a monovalent, bivalent, trivalent HSA-binding nanobody molecule disclosed in WO 2006/122786. In other embodiments, the HSA-binding SDAB molecule can be a monospecific or a multispecific molecule having at least one of the binding specificities bind to HSA. Exemplary TNFα-binding nanobodies include, but are not limited to, ALB1, humanized forms thereof (e.g., ALB6, ALB7, ALB8, ALB9, ALB10), disclosed in WO 06/122786.

In other embodiments, two or more of the single domain molecules of the SDAB molecules are fused, with or without a linking group, as a genetic or a polypeptide fusion. The linking group can be any linking group apparent to those of skill in the art. For instance, the linking group can be a biocompatible polymer with a length of 1 to 100 atoms. In one embodiment, the linking group includes or consists of polyglycine, polyserine, polylysine, polyglutamate, polyisoleucine, or polyarginine residues, or a combination thereof. For example, the polyglycine or polyserine linkers can include at least five, seven eight, nine, ten, twelve, fifteen, twenty, thirty, thirty-five and forty glycine and serine residues. Exemplary linkers that can be used include Gly-Ser repeats, for example, $(Gly)_4$-Ser repeats of at one, two, three, four, five, six, seven or more repeats (SEQ ID NO:8). In embodiments, the linker has the following sequences: $(Gly)_4$-Ser-$(Gly)_3$-Ser or $((Gly)_4$-Ser)n, where n is 4, 5, or 6 (SEQ ID NO:10).

The SDAB molecule separated or purified by the method or process of the invention can be further modified by associating, e.g., covalently or non-covalently a second moiety. For example, the nanobody molecule can be covalently attached to a suitable pharmacologically acceptable polymer, such as poly(ethyleneglycol) (PEG) or a derivative thereof (such as methoxypoly(ethyleneglycol) or mPEG). Examples of pegylated nanobody molecules are disclosed as TNF55-PEG40, TNF55-PEG60, TNF56-PEG40 and TNF56-PEG60 in WO 06/122786.

In one embodiment, the method or process further comprises one or more of ion (e.g., cation or anion) exchange chromatography, hydroxyapatite chromatography, affinity chromatography, size exclusion chromatography, hydrophobic interaction chromatography, metal affinity chromatography, diafiltration, ultrafiltration, and/or viral removal filtration.

In one embodiment, the method or process further includes preparing a formulation of the recombinant SDAB molecule as a pharmaceutical composition. The formulation can include the SDAB molecule alone or in combination with a second agent, e.g., a second therapeutically or pharmacologically active agent that is useful in treating a TNFa associated disorder, e.g., inflammatory or autoimmune disorders, including, but not limited to, rheumatoid arthritis (RA) (e.g., moderate to severe rheumatoid arthritis), arthritic conditions (e.g., psoriatic arthritis, polyarticular juvenile idiopathic arthritis (JIA), ankylosing spondylitis (AS), psoriasis, ulcerative colitis, Crohn's disease, inflammatory bowel disease, and/or multiple sclerosis. For example, the second agent may be an anti-TNF antibody or TNF binding fragment thereof, wherein the second TNF antibody binds to a different epitope than the TNF-binding SDAB molecule of the formulation. Other non-limiting examples of agents that can be co-formulated with the TNF-binding SDAB molecule include, but are not limited to, a cytokine inhibitor, a growth factor inhibitor, an immunosuppressant, an anti-inflammatory agent, a metabolic inhibitor, an enzyme inhibitor, a cytotoxic agent, and a cytostatic agent. In one embodiment, the additional agent is a standard treatment for arthritis, including, but not limited to, non-steroidal anti-inflammatory agents (NSAIDs); corticosteroids, including prednisolone, prednisone, cortisone, and triamcinolone; and disease modifying anti-rheumatic drugs (DMARDs), such as methotrexate, hydroxychloroquine (Plaquenil) and sulfasalazine, leflunomide (Arava®), tumor necrosis factor inhibitors, including etanercept (Enbrel®), infliximab (Remicade®) (with or without methotrexate), and adalimumab (Humira®), anti-CD20 antibody (e.g., Rituxan®), soluble interleukin-1 receptor, such as anakinra (Kineret®), gold, minocycline (Minocin®), penicillamine, and cytotoxic agents, including azathioprine, cyclophosphamide, and cyclosporine. Such combination therapies may advantageously utilize lower dosages of the administered therapeutic agents, thus avoiding possible toxicities or complications associated with the various monotherapies.

In another aspect, the invention features an SDAB molecule made by the method or process described herein. Compositions, e.g., pharmaceutical compositions and formulations, containing the SDAB molecules made by the method or process described herein are also encompassed by this invention. For example, the formulations may include the SDAB molecules described herein in a pharmaceutically acceptable carrier.

In one embodiment, the SDAB molecules made by method or process described herein are suitable for administration to a subject, e.g., a human subject (e.g., a patient having a TNFa associated disorder). For example, the SDAB molecule or formulation thereof can be administered to the subject by injection (e.g., subcutaneous, intravascular, intramuscular or intraperitoneal) or by inhalation.

In another aspect, the invention relates to methods for treating or preventing in a subject (e.g., a human subject) a disorder associated with an SDAB molecule described herein (e.g., a TNFa-associated disorder, e.g., inflammatory or autoimmune disorders, including, but not limited to, rheumatoid arthritis (RA) (e.g., moderate to severe rheumatoid arthritis), arthritic conditions (e.g., psoriatic arthritis, polyarticular juvenile idiopathic arthritis (JIA), ankylosing spondylitis (AS), psoriasis, ulcerative colitis, Crohn's disease, inflammatory bowel disease, and/or multiple sclerosis). The method includes administering to a subject, e.g., a human patient, a pharmaceutical composition includes a TNF-binding SDAB made by the method or process described herein, alone or in combination with any of the combination therapies described herein, in an amount such that one or more of the symptoms of the TNFα associated disorder are reduced.

In another aspect, the invention features a kit or an article of manufacture that includes a device, a syringe or a vial containing the SDAB made by the method or process described herein.

All publications, patent applications, patents, and other references mentioned herein are incorporated by reference in their entirety.

The details of one or more embodiments of the invention are set forth in the accompanying drawings and the description below. Other features, objects, and advantages of the invention will be apparent from the description and figures, and from the claims.

BRIEF DESCRIPTION OF THE DRAWINGS

FIG. 2 depicts the amino acid sequence of ATN-103 polypeptide chain (SEQ ID NO:1).

FIG. 4A depicts the amino acid sequence of full length Staphylococcal Protein A (SpA) (SEQ ID NO:11). FIG. 4B depicts the amino acid sequence of modified domain B of SpA (SEQ ID NO:12). The α-helix regions are indicated in bold.

DETAILED DESCRIPTION

Figure 1:
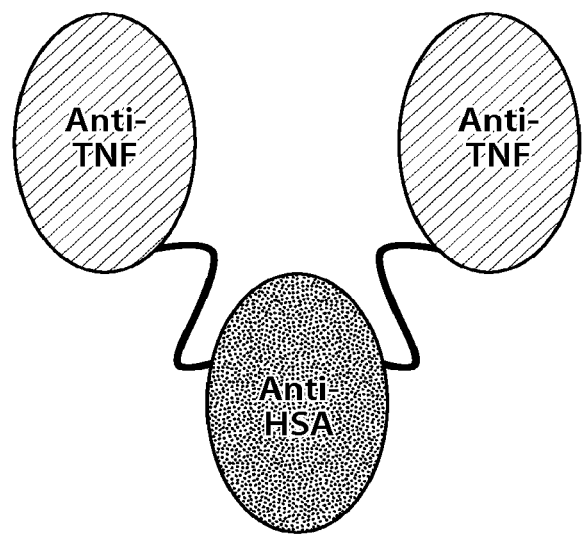
FIG. 1 depicts a schematic diagram of the predicted structure of ATN-103.

The present invention is based, at least in part, on the discovery that an SDAB molecule that includes one or more single binding domains (e.g., one or more nanobody molecules) interacts with, e.g., binds to, Protein A or a functional variant thereof, thereby enabling the use of Protein A-based affinity modalities of chromatography in the purification of the SDAB molecule. Thus, the present invention relates to processes and methods of purifying or separating antigen-binding fusion polypeptides that include one or more single binding domains (e.g., one or more nanobody molecules), devoid of a complementary antibody domain and an immunoglobulin Fc region, using Protein A-based affinity chromatography.

In order that the present invention may be more readily understood, certain terms are first defined. Additional definitions are set forth throughout the detailed description.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

The terms "proteins" and "polypeptides" are used interchangeably herein.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

The term "SDAB molecule preparation" refers to any composition containing a SDAB molecule and/or one or more unwanted contaminants. The preparation may be partially separated or purified, e.g., by passing through a chromatographic column as described herein, e.g., a Protein A-based or cation exchange support.

The term "chromatography" refers to the separation of chemically different molecules in a mixture from one another by contacting the mixture with an adsorbent, wherein one class of molecules reversibly binds to or is adsorbed onto the adsorbent. Molecules that are least strongly adsorbed to or retained by the adsorbent are released from the adsorbent under conditions where those more strongly adsorbed or retained are not.

The term "flow-through mode" refers to an SDAB molecule preparation separation technique in which at least one SDAB molecule contained in the preparation is intended to flow through a chromatographic resin or support, while at least one potential contaminant or impurity binds to the chromatographic resin or support. Flow-through mode may be used, for instance, in hydroxyapatite chromatography and ion exchange chromatography.

"Binding mode" refers to an SDAB molecule preparation separation technique in which at least one antibody molecule contained in the preparation binds to a chromatographic resin or support, while at least one contaminant or impurity flows through. Binding mode may be used, for instance, in hydroxyapatite chromatography and ion exchange chromatography.

A "contaminant" refers to any foreign or objectionable molecule, particularly a biological macromolecule such as a DNA, an RNA, or a protein, other than the protein being purified that is present in a sample of a protein being purified. Contaminants include, for example, other host cell proteins from cells used to recombinantly express the protein being purified, proteins that are part of an absorbent used in an affinity chromatography step that may leach into a sample during prior affinity chromatography step, such as Protein A, and mis-folded variants of the target protein itself.

"Host cell proteins" include proteins encoded by the naturally-occurring genome of a host cell into which DNA encoding a protein that is to be purified is introduced. Host cell proteins may be contaminants of the protein to be purified, the levels of which may be reduced by purification. Host cell proteins can be assayed for by any appropriate method including gel electrophoresis and staining and/or ELISA assay, among others. Host cell proteins include, for example, Chinese Hamster Ovary (CHO) proteins (CHOP) produced as a product of expression of recombinant proteins.

The term "high molecular weight aggregates" or "HMWA" refers to an association of at least two antibody molecules. The association may arise by any method including, but not limited to, covalent, non-covalent, disulfide, or nonreducible crosslinking. The at least two molecules may bind to the same or different antigens.

As used herein, the term "Protein A" and associated phrases, such as "Protein A-based support" are intended to include Protein A (e.g., recombinant or isolated Protein A), or a functional variant thereof. In one embodiment, the Protein A is full length Staphylococcal Protein A (SpA) composed of five domains of about 50-60 amino acid residues known as E, D, A, B and C domains in order from the N-terminus. (Sjodhal *Eur J Biochem* 78: 471-490 (1977); Uhlen et al. *J. Biol. Chem.* 259: 1695-1702 (1984)). These domains contain approximately 58 residues, each sharing about 65%-90% amino acid sequence identity. Binding studies between Protein A and antibodies have shown that while all five domains of SpA (E, D, A, B and C) bind to an IgG via its Fc region, domains D and E exhibit significant Fab binding (Ljungberg et al. *Mol. Immunol.* 30(14):1279-1285 (1993); Roben et al. *J. Immunol.* 154: 6437-6445 (1995); Starovasnik et al. *Protein Sci* 8:1423-1431 (1999). The Z-domain, a functional analog and energy-minimized version of the B domain (Nilsson et al. *Protein Eng* 1:107-113 (1987)) was shown to have negligible binding to the antibody variable domain region (Cedergren et al. *Protein Eng* 6(4):441-448 (1993); Ljungberg et al. (1993) supra; Starovasnik et al. (1999) supra). Protein A can include the amino acid sequence of SpA (SEQ ID NO:11) shown in FIG. 4A, or an amino acid sequence substantially identical thereto. In other embodiments, the Protein A is a functional variant of SpA that includes at least one domain chosen from E, D, A, B and/or C, or a modified form thereof. For example, the functional variant of SpA can include at least domain B of SpA, or a variant of domain B, having one or more substituted asparagine residues, also referred to herein as domain Z. In one embodiment, the functional variant of SpA includes the amino acid sequence of SEQ ID NO:12) shown in FIG. 4B, or an amino acid sequence substantially identical thereto. Other permutations of functional variants of Protein A can be used comprising domain B, or a variant domain B, and one or more of: domains A and/or C; domains E, A and/or C; or domains E, D, A and/or C. Any combination of E, D, A, B and/or C, or a functional variant thereof, can be used as long as the combination is capable of binding to the SDAB molecule.

"Ceramic hydroxyapatite" or 'cHA' refers to an insoluble hydroxylated calcium phosphate, e.g., having the formula [$CaO(PO_4)_6(OH)_2$ or $Ca_{10}(PO_4)_6(OH)_2$], which has been sintered at high temperatures into a spherical, macroporous ceramic form. The term "cHA" encompasses, but is not limited to, Type I and Type II ceramic hydroxyapatite. Unless specified, "cHA" refers to any particle size: including, but not limited to, 20, 40, and 80 μm.

To "purify" a polypeptide means to reduce the amounts of foreign or objectionable elements, especially biological macromolecules such as proteins or DNA, that may be present in a sample of the protein. The presence of foreign proteins may be assayed by any appropriate method including gel electrophoresis and staining and/or ELISA assay. The presence of DNA may be assayed by any appropriate method including gel electrophoresis and staining and/or assays employing polymerase chain reaction. In embodiments, the polypeptide, e.g., the SDAB molecule, is purified to at least 85%, 90%, 95%, 96%, 97%, 98%, 99% or higher purity.

A polypeptide is "separated" (or "removed") from a mixture comprising the protein and other contaminants when the mixture is subjected to a process such that the concentration of the target polypeptide is higher in the resulting product than the starting product.

The methods and compositions of the present invention encompass polypeptides having the sequences specified, or sequences substantially identical or similar thereto, e.g., sequences at least 85%, 90%, 95% identical or higher to the sequence specified. In the context of an amino acid sequence, the term "substantially identical" is used herein to refer to a first amino acid that contains a sufficient or minimum number of amino acid residues that are i) identical to, or ii) conservative substitutions of aligned amino acid residues in a second amino acid sequence such that the first and second amino acid sequences can have a common structural domain and/or common functional activity. For example, amino acid sequences containing a common structural domain having at least about 85%, 90%. 91%, 92%, 93%, 94%, 95%, 96%, 97%, 98% or 99% identity to a reference sequence.

Also included as polypeptides of the present invention are fragments, derivatives, analogs, or variants of the foregoing polypeptides, and any combination thereof. The terms "fragment," "variant," "derivative" and "analog" when referring to proteins of the present invention include any polypeptides which retain at least some of the functional properties of the corresponding native antibody or polypeptide. Fragments of polypeptides of the present invention include proteolytic fragments, as well as deletion fragments, in addition to specific antibody fragments discussed elsewhere herein. Variants of the polypeptides of the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques. Variant polypeptides may comprise conservative or non-conservative amino acid substitutions, deletions or additions. Derivatives of the fragments of the present invention are polypeptides which have been altered so as to exhibit additional features not found on the native polypeptide. Examples include fusion proteins. Variant polypeptides may also be referred to herein as "polypeptide analogs." As used herein a "derivative" of a polypeptide refers to a subject polypeptide having one or more residues chemically derivatized by reaction of a functional side group. Also included as "derivatives" are those polypeptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

The term "functional variant" refers polypeptides that have a substantially identical amino acid sequence to the naturally-occurring sequence, or are encoded by a substantially identical nucleotide sequence, and are capable of having one or more activities of the naturally-occurring sequence.

Calculations of homology or sequence identity between sequences (the terms are used interchangeably herein) are performed as follows.

To determine the percent identity of two amino acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues at corresponding amino acid positions are then compared. When a position in the first sequence is occupied by the same amino acid residue as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch ((1970) *J. Mol. Biol.* 48:444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller ((1989) CABIOS, 4:11-17) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215: 403-10. BLAST nucleotide searches can be performed with the NBLAST program, score=100, wordlength=12 to obtain nucleotide sequences homologous to a nucleic acid (SEQ ID NO:1) molecules of the invention. BLAST protein searches can be performed with the XBLAST program, score=50, wordlength=3 to obtain amino acid sequences homologous to a protein (SEQ ID NO:1) protein molecules of the invention. To obtain gapped alignments for comparison purposes, Gapped BLAST can be utilized as described in Altschul et al., (1997) *Nucleic Acids Res.* 25:3389-3402. When utilizing BLAST and Gapped BLAST programs, the default parameters of the respective programs (e.g., XBLAST and NBLAST) can be used.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Various aspects of the invention are described in further detail below.

Single Domain Antigen Binding (SDAB) Molecules

In certain embodiments, the SDAB molecules purified by the methods of the invention are single chain fusion polypeptides comprised of one or more nanobody molecules. For example, the SDAB molecule can be a single chain fusion polypeptide comprising one or more nanobody molecules, that binds to one or more target antigens connected via a linker, e.g., a peptide linker.

As used herein, a "fusion polypeptide" refers to a protein containing two or more operably associated, e.g., linked, moieties, e.g., protein moieties. Typically, the moieties are covalently associated. The moieties can be directly associated, or connected via a spacer or linker (e.g., a linking group as described herein). A fusion polypeptide can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) *Current Protocols in Molecular Biology*, John Wiley & Sons, 1992). Moreover, many expression vectors are commercially available that encode a fusion moiety. In some embodiments, fusion polypeptides exist as oligomers, such as dimers or trimers of a single contiguous polypeptides, or two or more non-contiguous polypeptides. In other embodiments, additional amino acid sequences can be added to the N- or C-terminus of the fusion protein to facilitate expression, steric flexibility, detection and/or isolation or purification.

Single domain antigen binding (SDAB) molecules include molecules whose complementary determining regions are part of a single domain polypeptide. Examples include, but are not limited to, heavy chain variable domains, binding molecules naturally devoid of light chains, single domains derived from conventional 4-chain antibodies, engineered domains and single domain scaffolds other than those derived from antibodies. SDAB molecules may be any of the art, or any future single domain molecules. SDAB molecules may be derived from any species including, but not limited to mouse, human, camel, llama, fish, shark, goat, rabbit, and bovine. This term also includes naturally occurring single domain antibody molecules from species other that Camelidae and sharks.

In one aspect of the invention, an SDAB molecule can be derived from a variable region of the immunoglobulin found in fish, such as, for example, that which is derived from the immunoglobulin isotype known as Novel Antigen Receptor (NAR) found in the serum of shark. Methods of producing single domain molecules derived from a variable region of NAR ("IgNARs") are described in WO 03/014161 and Streltsov (2005) *Protein Sci.* 14:2901-2909.

According to another aspect of the invention, an SDAB molecule is a naturally occurring single domain antigen binding molecule known as heavy chain devoid of light chains. Such single domain molecules are disclosed in WO 9404678 and Hamers-Casterman, C. et al. (1993) *Nature* 363:446-448, for example. For clarity reasons, this variable domain derived from a heavy chain molecule naturally devoid of light chain is known herein as a VHH or nanobody to distinguish it from the conventional VH of four chain immunoglobulins. Such a VHH molecule can be derived from Camelidae species, for example in camel, llama, dromedary, alpaca and guanaco. Other species besides Camelidae may produce heavy chain molecules naturally devoid of light chain; such VHHs are within the scope of the invention.

In certain embodiments, the SDAB molecule includes at least one immunoglobulin variable domain (including one, two and/or three complementarity determining regions (CDRs)), in the absence of a complementary antibody variable chain (e.g., a heavy chain variable region (VH) in the absence of the corresponding light chain variable region (VL)), and/or an immunoglobulin constant region, e.g., an Fc region (or a constant region or a portion thereof capable of binding to Protein A).

In certain embodiments, an SDAB molecule does not include antibody molecules having a heavy and light antibody variable domains or chains (e.g., full length antibodies), or antigen-binding fragments thereof having heavy and light antibody fragments (e.g., Fab, F(ab')$_2$ fragment, scFv having a light and heavy chain variable regions in a single polypeptide chain, or a Fv fragment consisting of the VL and VH domains of a single arm of an antibody).

The SDAB molecules can be recombinant, CDR-grafted, humanized, camelized, de-immunized and/or in vitro generated (e.g., selected by phage display), as described in more detail below.

The term "antigen-binding" is intended to include the part of a polypeptide, e.g., a single domain molecule described herein, that comprises determinants that form an interface that binds to a target antigen, or an epitope thereof. With respect to proteins (or protein mimetics), the antigen-binding site typically includes one or more loops (of at least four amino acids or amino acid mimics) that form an interface that binds to the target antigen. Typically, the antigen-binding site of the polypeptide, e.g., the single domain antibody molecule, includes at least one or two CDRs, or more typically at least three, four, five or six CDRs.

The VH and VL regions can be subdivided into regions of hypervariability, termed "complementarity determining regions" (CDR), interspersed with regions that are more conserved, termed "framework regions" (FR). The extent of the framework region and CDRs has been precisely defined by a number of methods (see, Kabat, E. A., et al. (1991) *Sequences of Proteins of Immunological Interest*, Fifth Edition, U.S. Department of Health and Human Services, NIH Publication No. 91-3242; Chothia, C. et al. (1987) *J. Mol. Biol.* 196:901-917; and the AbM definition used by Oxford Molecular's AbM antibody modelling software. See, generally, e.g., *Protein Sequence and Structure Analysis of Antibody Variable Domains*. In: Antibody Engineering Lab Manual (Ed.: Duebel, S. and Kontermann, R., Springer-Verlag, Heidelberg). Generally, unless specifically indicated, the following definitions are used: AbM definition of CDR1 of the heavy chain variable domain and Kabat definitions for the other CDRs. In addition, embodiments of the invention described with respect to Kabat or AbM CDRs may also be implemented using Chothia hypervariable loops. Each VH and VL typically includes three CDRs and four FRs, arranged from amino-terminus to carboxy-terminus in the following order: FR1, CDR1, FR2, CDR2, FR3, CDR3, FR4.

The term "immunoglobulin variable domain" is frequently understood in the art as being identical or substantially identical to a VL or a VH domain of human or animal origin. It shall be recognized that immunoglobulin variable domain may have evolved in certain species, e.g., sharks and llama, to differ in amino acid sequence from human or mammalian VL or VH. However, these domains are primarily involved in antigen binding. The term "immunoglobulin variable domain" typically includes at least one or two CDRs, or more typically at least three CDRs.

A "constant immunoglobulin domain" or "constant region" is intended to include an immunoglobulin domain that is identical to or substantially similar to a CL, CH1, CH2, CH3, or CH4, domain of human or animal origin. See e.g. Charles A Hasemann and J. Donald Capra, *Immunoglobulins: Structure and Function*, in William E. Paul, ed., *Fundamental Immunology*, Second Edition, 209, 210-218 (1989). The term "Fc region" refers to the Fc portion of the constant immunoglobulin domain that includes immunoglobulin domains CH2 and CH3 or immunoglobulin domains substantially similar to these.

In certain embodiments, the SDAB molecule is a monovalent, or a multispecific molecule (e.g., a bivalent, trivalent, or tetravalent molecule). In other embodiments, the SDAB molecule is a monospecific, bispecific, trispecific or tetraspecific molecule. Whether a molecule is "monospecific" or "multispecific," e.g., "bispecific," refers to the number of different epitopes with which a binding polypeptide reacts. Multispecific molecules may be specific for different epitopes of a target polypeptide described herein or may be specific for a target polypeptide as well as for a heterologous epitope, such as a heterologous polypeptide or solid support material.

As used herein the term "valency" refers to the number of potential binding domains, e.g., antigen binding domains, present in an SDAB molecule. Each binding domain specifically binds one epitope. When an SDAB molecule comprises more than one binding domain, each binding domain may specifically bind the same epitope, for an antibody with two binding domains, termed "bivalent monospecific," or to different epitopes, for an SDAB molecule with two binding domains, termed "bivalent bispecific." An SDAB molecule may also be bispecific and bivalent for each specificity (termed "bispecific tetravalent molecules"). Bispecific bivalent molecules, and methods of making them, are described, for instance in U.S. Pat. Nos. 5,731,168; 5,807,706; 5,821,333; and U.S. Appl. Publ. Nos. 2003/020734 and 2002/0155537, the disclosures of all of which are incorporated by reference herein. Bispecific tetravalent molecules, and methods of making them are described, for instance, in WO 02/096948 and WO 00/44788, the disclosures of both of which are incorporated by reference herein. See generally, PCT publications WO 93/17715; WO 92/08802; WO 91/00360; WO 92/05793; Tutt et al., *J. Immunol.* 147:60-69 (1991); U.S. Pat. Nos. 4,474,893; 4,714,681; 4,925,648; 5,573,920; 5,601,819; Kostelny et al., *J. Immunol.* 148: 1547-1553 (1992).

In certain embodiments, the SDAB molecule is a single chain fusion polypeptide comprising one or more single domain molecules (e.g., nanobodies), devoid of a complementary variable domain or an immunoglobulin constant, e.g., Fc, region, that binds to one or more target antigens. An exemplary target antigen recognized by the antigen-binding polypeptides includes tumor necrosis factor α (TNF α). In certain embodiments, the antigen-binding single domain molecule binds to a serum protein, e.g., a human serum proteins chosen from one or more of serum albumin (human serum albumin (HSA)) or transferin.

TNFα

Tumor necrosis factor alpha is known in the art to the associated with inflammatory disorders such as rheumatoid arthritis, Crohn's disease, ulcerative colitis and multiple sclerosis. Both and the receptors (CD120a and CD120b) have been studied in great detail. TNFa TNFa in its bioactive form is a trimer. Several strategies to antagonize the action of TNFa using anti-TNFa antibodies have been developed and are currently commercially available, such as Remicade® and Humira®. Antibody molecules against TNFa are known. Numerous examples of TNFa-binding single domain antigen binding molecules (e.g., nanobodies) are disclosed in WO 2004/041862, WO 2004/041865, WO 2006/122786, the contents of all of which are incorporated by reference herein in their entirety. Additional examples of single domain antigen binding molecules are disclosed in US 2006/286066, US 2008/0260757, WO 06/003388, U.S. Ser. No. 05/027,1663, U.S. Ser. No. 06/010,6203, the contents of all of which are incorporated by reference herein in their entirety. In other embodiments, mono-, bi-, tri- and other multi-specific single domain antibodies against TNFa and a serum protein, e.g., HSA, are disclosed in these references.

In specific embodiments, the TNFα-binding nanobody molecule comprises one or more of the nanobodies disclosed in WO 2006/122786. For example, the TNFα-binding nanobody molecule can be a monovalent, bivalent, trivalent TNFα-binding nanobody molecule disclosed in WO 2006/122786. Exemplary TNFα-binding nanobodies include, but are not limited to, TNF1, TNF2, TNF3, humanized forms thereof (e.g., TNF29, TNF30, TNF31, TNF32, TNF33). Additional examples of monovalent TNFα-binding nanobodies are disclosed in Table 8 of WO 2006/122786. Exemplary bivalent TNFα-binding nanobody molecules include, but are not limited to, TNF55 and TNF56, which comprise two TNF30 nanobodies linked via a peptide linker to form a single fusion polypeptide (disclosed in WO 2006/122786). Additional examples of bivalent TNFα-binding nanobody molecules are disclosed in Table 19 of WO 2006/122786 as TNF4, TNF5, TNF6, TNF7, TNF8).

In other embodiments, the HSA-binding nanobody molecule comprises one or more of the nanobodies disclosed in WO 2006/122786. For example, the HSA-binding nanobody molecule can be a monovalent, bivalent, trivalent HSA-binding nanobody molecule disclosed in WO 2006/122786. In other embodiments, the HSA-binding nanobody molecule can be a monospecific or a multispecific molecule having at least one of the binding specificities bind to HSA. Exemplary TNFα-binding nanobodies include, but are not limited to, ALB1, humanized forms thereof (e.g., ALB6, ALB7, ALB8, ALB9, ALB10), disclosed in WO 06/122786.

In other embodiments, two or more of the single domain molecules of the nanobody molecules are fused, with or without a linking group, as a genetic or a polypeptide fusion. The linking group can be any linking group apparent to those of skill in the art. For instance, the linking group can be a biocompatible polymer with a length of 1 to 100 atoms. In one embodiment, the linking group includes or consists of polyglycine, polyserine, polylysine, polyglutamate, polyisoleucine, or polyarginine residues, or a combination thereof. For example, the polyglycine or polyserine linkers can include at least five, seven eight, nine, ten, twelve, fifteen, twenty, thirty, thirty-five and forty glycine and serine residues. Exemplary linkers that can be used include Gly-Ser repeats, for example, (Gly)$_4$-Ser repeats of at one, two, three, four, five, six, seven or more repeats (SEQ ID NO:8). In embodiments, the linker has the following sequences:

(Gly)$_4$-Ser-(Gly)$_3$-Ser (SEQ ID NO:9) or ((Gly)$_4$-Ser)n, where n is 4, 5, or 6 (SEQ ID NO:10).

In one exemplary embodiment, an antigen-binding polypeptide composed of a single chain polypeptide fusion of two single domain antibody molecules (e.g., two camelid variable regions) that bind to a target antigen, e.g., tumor necrosis factor (TNFαa), and one single domain antibody molecule (e.g., a camelid variable region) that binds to a serum protein, e.g., HSA, referred to herein as "ATN-103," was shown to bind to Protein A, or a functional variant thereof. ATN-103 is a humanized, trivalent, bispecific, TNFa-inhibiting fusion protein. The antigen for this protein is tumor necrosis factor-alpha (TNF). FIG. 1 provides a schematic representation of the predicted structure of ATN-103. This fusion protein is derived from camelids and has a high degree of sequence and structural homology to human immunoglobulin VH domains. Its single polypeptide chain is composed of two binding domains to TNFα and one to human serum albumin (HSA), with two nine amino acid G-S linkers connecting the domains. A detailed description of ATN-103 is provided in WO 06/122786.

The complete amino acid sequence of the ATN-103 polypeptide chain predicted from the DNA sequence of the corresponding expression vector is shown in FIG. 2 (SEQ ID NO:1) (residues are numbered starting with the NH$_2$-terminus as Residue Number 1). The last amino acid residue encoded by the DNA sequence is S$^{363}$ and constitutes the COOH-terminus of the protein. The predicted molecular mass for disulfide-bonded ATN-103 (with no posttranslational modifications) is 38434.7 Da. ATN-103 contains no N-linked glycosylation consensus sequence. The molecular mass observed for the predominant isoform by nanoelectrospray ionization quadrupole time-of-flight mass spectrometry corresponds to 38433.9 Da confirming the absence of post-translational modifications.

In FIG. 2, complementarity determining regions (CDR) are underlined (SEQ ID NOs:2-7). The predicted intramolecular disulfide bonds are illustrated by connections of the cysteine residues involved. The binding domains to TNF are shown in bold and the binding domain to HSA is shown in bold italics. The amino acid linkers connecting these binding domains are in italics. The signal peptide ($^{-19}$MGW . . . VHS$^{-1}$) is also shown for the polypeptide chain.

Preparation of SDAB Molecules

The SDAB molecules may comprised of one or more single domain molecules (e.g., nanobodies) that are recombinant, CDR-grafted, humanized, camelized, de-immunized, and/or in vitro generated (e.g., selected by phage display). Techniques for generating antibodies and SDAB molecules, and modifying them recombinantly are known in the art and are described in detail below.

Numerous methods known to those skilled in the art are available for obtaining antibodies. For example, monoclonal antibodies may be produced by generation of hybridomas in accordance with known methods. Hybridomas formed in this manner are then screened using standard methods, such as enzyme-linked immunosorbent assay (ELISA) and surface plasmon resonance (BIACORE™) analysis, to identify one or more hybridomas that produce an nanobody that specifically binds with a specified antigen. Any form of the specified antigen may be used as the immunogen, e.g., recombinant antigen, naturally occurring forms, any variants or fragments thereof, as well as antigenic peptide thereof.

One exemplary method of making antibodies and SDAB molecules includes screening protein expression libraries, e.g., phage or ribosome display libraries. Phage display is described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; and WO 90/02809.

In addition to the use of display libraries, the specified antigen can be used to immunize a non-human animal, e.g., a rodent, e.g., a mouse, hamster, or rat. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XENOMOUSE™, Green et al. (1994) *Nature Genetics* 7:13-21, US 2003-0070185, WO 96/34096, published Oct. 31, 1996, and PCT Application No. PCT/US96/05928, filed Apr. 29, 1996.

In another embodiment, an SDAB molecule is obtained from the non-human animal, and then modified, e.g., humanized, deimmunized, chimeric, may be produced using recombinant DNA techniques known in the art. A variety of approaches for making chimeric antibodies and SDAB molecules have been described. See e.g., Morrison et al., *Proc. Natl. Acad. Sci. U.S.A.* 81:6851, 1985; Takeda et al., *Nature* 314:452, 1985, Cabilly et al., U.S. Pat. No. 4,816,567; Boss et al., U.S. Pat. No. 4,816,397; Tanaguchi et al., European Patent Publication EP171496; European Patent Publication 0173494, United Kingdom Patent GB 2177096B. Humanized antibodies and SDAB molecules may also be produced, for example, using transgenic mice that express human heavy and light chain genes, but are incapable of expressing the endogenous mouse immunoglobulin heavy and light chain genes. Winter describes an exemplary CDR-grafting method that may be used to prepare the humanized antibodies and SDAB molecule described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody and SDAB molecule to a predetermined antigen.

Humanized antibodies can be generated by replacing sequences of the Fv variable domain that are not directly involved in antigen binding with equivalent sequences from human Fv variable domains. Exemplary methods for generating humanized antibodies or fragments thereof are provided by Morrison (1985) *Science* 229:1202-1207; by Oi et al. (1986) *BioTechniques* 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an nanobody against a predetermined target, as described above, as well as from other sources. The recombinant DNA encoding the humanized SDAB molecule, e.g., nanobody molecule, can then be cloned into an appropriate expression vector.

In certain embodiments, a humanized SDAB molecule, e.g., nanobody molecule, is optimized by the introduction of conservative substitutions, consensus sequence substitutions, germline substitutions and/or backmutations. Such altered immunoglobulin molecules can be made by any of several techniques known in the art, (e.g., Teng et al., *Proc. Natl. Acad. Sci. U.S.A.*, 80: 7308-7312, 1983; Kozbor et al., *Immunology Today*, 4: 7279, 1983; Olsson et al., *Meth.*

*Enzymol.*, 92: 3-16, 1982), and may be made according to the teachings of PCT Publication WO92/06193 or EP 0239400).

Techniques for humanizing SDAB molecules, e.g., nanobody molecules, are disclosed in WO 06/122786.

An SDAB molecule, e.g., nanobody molecule, may also be modified by specific deletion of human T cell epitopes or "deimmunization" by the methods disclosed in WO 98/52976 and WO 00/34317. Briefly, the heavy and light chain variable domains of, e.g., a nanobody can be analyzed for peptides that bind to MHC Class II; these peptides represent potential T-cell epitopes (as defined in WO 98/52976 and WO 00/34317). For detection of potential T-cell epitopes, a computer modeling approach termed "peptide threading" can be applied, and in addition a database of human MHC class II binding peptides can be searched for motifs present in the $V_H$ and $V_L$ sequences, as described in WO 98/52976 and WO 00/34317. These motifs bind to any of the 18 major MHC class II DR allotypes, and thus constitute potential T cell epitopes. Potential T-cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences, e.g., are disclosed in Tomlinson, et al. (1992) *J. Mol. Biol.* 227:776-798; Cook, G. P. et al. (1995) *Immunol. Today* Vol. 16 (5): 237-242; Chothia, D. et al. (1992) *J. Mol. Biol.* 227:799-817; and Tomlinson et al. (1995) *EMBO J.* 14:4628-4638. The V BASE directory provides a comprehensive directory of human immunoglobulin variable region sequences (compiled by Tomlinson, I. A. et al. MRC Centre for Protein Engineering, Cambridge, UK). These sequences can be used as a source of human sequence, e.g., for framework regions and CDRs. Consensus human framework regions can also be used, e.g., as described in U.S. Pat. No. 6,300,064.

The SDAB molecules, e.g., nanobody molecules, can be produced by living host cells that have been genetically engineered to produce the protein. Methods of genetically engineering cells to produce proteins are well known in the art. See e.g. Ausabel et al., eds. (1990), *Current Protocols in Molecular Biology* (Wiley, New York). Such methods include introducing nucleic acids that encode and allow expression of the protein into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5a, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and WI38. New animal cell lines can be established using methods well know by those skilled in the art (e.g., by transformation, viral infection, and/or selection). Optionally, the protein can be secreted by the host cells into the medium.

Modified SDAB Molecules

The SDAB molecule, e.g., nanobody molecule, purified using the methods of the invention can have an amino acid sequence that differs at at least one amino acid position in one of the framework regions from the amino acid sequence of a naturally occurring domain, e.g., VH domain.

It shall be understood that the amino acid sequences of the some of the SDAB molecules of the invention, such as the humanized SDAB molecules, can differ at at least one amino acid position in at least one of the framework regions from the amino acid sequences of naturally occurring domain, e.g., a naturally occurring VHI-I domains.

The invention also includes methods of purifying derivatives of the SDAB molecules. Such derivatives can generally be obtained by modification, and in particular by chemical and/or biological (e.g enzymatical) modification, of the SDAB molecules and/or of one or more of the amino acid residues that form the SDAB molecules disclosed herein.

Examples of such modifications, as well as examples of amino acid residues within the SDAB molecule sequence that can be modified in such a manner (i.e. either on the protein backbone but preferably on a side chain), methods and techniques that can be used to introduce such modifications and the potential uses and advantages of such modifications will be clear to the skilled person.

For example, such a modification may involve the introduction (e.g. by covalent linking or in an other suitable manner) of one or more functional groups, residues or moieties into or onto the SDAB molecule, and in particular of one or more functional groups, residues or moieties that confer one or more desired properties or functionalities to the SDAB molecules. Example of such functional groups will be clear to the skilled person.

For example, such modification may comprise the introduction (e.g. by covalent binding or in any other suitable manner) of one or more functional groups that that increase the half-life, the solubility and/or the absorption of the SDAB molecule, that reduce the immunogenicity and/or the toxicity of the SDAB molecule, that eliminate or attenuate any undesirable side effects of the SDAB molecule, and/or that confer other advantageous properties to and/or reduce the undesired properties of the SDAB molecule; or any combination of two or more of the foregoing. Examples of such functional groups and of techniques for introducing them will be clear to the skilled person, and can generally comprise all functional groups and techniques mentioned in the general background art cited hereinabove as well as the functional groups and techniques known per se for the modification of pharmaceutical proteins, and in particular for the modification of antibodies or antibody fragments (including ScFv's and-148-single domain antibodies), for which reference is for example made to Remington's Pharmaceutical Sciences, 16th ed., Mack Publishing Co., Easton, Pa. (1980). Such functional groups may for example be linked directly (for example covalently) to a Nanobody of the invention, or optionally via a suitable linker or spacer, as will again be clear to the skilled person.

One widely used techniques for increasing the half-life and/or the reducing immunogenicity of pharmaceutical proteins comprises attachment of a suitable pharmacologically acceptable polymer, such as poly(ethyleneglycol) (PEG) or derivatives thereof (such as methoxypoly(ethyleneglycol) or mPEG). Generally, any suitable form of pegylation can be used, such as the pegylation used in the art for antibodies and antibody fragments (including but not limited to (single) domain antibodies and ScFv's); reference is made to for example Chapman, *Nat. Biotechnol.*, 54, 531-545 (2002); by Veronese and Harris, *Adv. Drug Deliv. Rev.* 54, 453-456 (2003), by Harris and Chess, *Nat. Rev. Drug. Discov.*, 2, (2003) and in WO 04/060965. Various reagents for pegylation of proteins are also commercially available, for example from Nektar Therapeutics, USA.

Preferably, site-directed pegylation is used, in particular via a cysteine-residue (see for example Yang et al., *Protein Engineering*, 16, 10, 761-770 (2003). For example, for this purpose, PEG may be attached to a cysteine residue that naturally occurs in an SDAB molecule, an SDAB molecule may be modified so as to suitably introduce one or more cysteine residues for attachment of PEG, or an amino acid sequence comprising one or more cysteine residues for attachment of PEG may be fused to the N- and/or C-terminus of a Nanobody of the invention, all using techniques of protein engineering known per se to the skilled person.

Preferably, for the SDAB molecule, a PEG is used with a molecular weight of more than 5000, such as more than 10,000 and less than 200,000, such as less than 100,000; for example in the range of 20,000-80,000.

With regard to pegylation, its should be noted that generally, the invention also encompasses any SDAB molecule that has been pegylated at one or more amino acid positions, preferably in such a way that said pegylation either (1) increases the half-life in vivo; (2) reduces immunogenicity; (3) provides one or more further beneficial properties known per se for pegylation; (4) does not essentially affect the affinity of the SDAB molecule (e.g. does not reduce said affinity by more than 90%, preferably not by more than 50%, and by no more than 10%, as determined by a suitable assay, such as those described in the Examples below); and/or (4) does not affect any of the other desired properties of the SDAB molecule. Suitable PEG-groups and methods for attaching them, either specifically or non-specifically, will be clear to the skilled person.

Suitable kits and reagents for such pegylation can for example be obtained from Nektar (CA, USA).

Another, usually less preferred modification comprises N-linked or O-linked glycosylation, usually as part of co-translational and/or post-translational modification, depending on the host cell used for expressing the SDAB molecule.

Chromatographic Processes

The process of purifying a protein often requires numerous steps, with each step resulting in a further reduction in yield. Protein A-based chromatography is one of many techniques commonly used. Protein purification by Protein A-based chromatography may be performed in a column containing an immobilized Protein A ligand (typically a column packed with modified support of methacrylate copolymer or agarose beads to which is affixed an adsorbent consisting of Protein A or functional derivatives thereof). The column is typically equilibrated with a buffer at high salt concentration and a sample containing a mixture of proteins (the target protein, plus contaminating proteins) in a compatible non-denaturing high salt solution, is loaded onto the column. As the mixture passes through the column, the target protein binds to the adsorbent within the column, while unbound contaminants flow through. Bound protein is then eluted from the column with a reduced salt concentration. Typically, the target protein may be recovered by eluting the column with a salt concentration applied in a gradual or step-wise reduced gradient, to selectively release the various bound proteins at the particular salt concentration conducive to their release, and collecting discreet fractions until the fraction containing the more purified protein is obtained. By collecting flow-through fractions over discreet periods of time, fractions containing specific proteins can be isolated. In a process where a target protein is bound to the column (while allowing contaminants to flow through), adsorbents having greater affinity to Protein A are typically used to bind a broader range of proteins which will be collected in a specific fraction conducive to the release of the protein.

The process of the invention can be used in combination with other protein purification methodologies, such as salt precipitation, affinity chromatography, hydroxyapatite chromatography, reverse phase liquid chromatography, ion-exchange chromatography, or any other commonly used protein purification technique. It is contemplated, however, that the process of the present invention will eliminate or significantly reduce the need for other purification steps.

Any or all chromatographic steps of the present invention can be carried out by any mechanical means. Chromatography may be carried out, for example, in a column. The column may be run with or without pressure and from top to bottom or bottom to top. The direction of the flow of fluid in the column may be reversed during the chromatography process. Chromatography may also be carried out using a batch process in which the solid media is separated from the liquid used to load, wash, and elute the sample by any suitable means, including gravity, centrifugation, or filtration. Chromatography may also be carried out by contacting the sample with a filter that absorbs or retains some molecules in the sample more strongly than others. In the following description, the various embodiments of the present invention are described in the context of chromatography carried out in a column. It is understood, however, that use of a column is merely one of several chromatographic modalities that may be used, and the illustration of the present invention using a column does not limit the application of the present invention to column chromatography, as those skilled in the art may readily apply the teachings to other modalities as well, such as those using a batch process or filter.

Suitable supports may be any currently available or later developed materials having the characteristics necessary to practice the claimed method, and may be based on any synthetic, organic, or natural polymers. For example, commonly used support substances include organic materials such as cellulose, polystyrene, agarose, sepharose, polyacrylamide polymethacrylate, dextran and starch, and inorganic materials, such as charcoal, silica (glass beads or sand) and ceramic materials. Suitable solid supports are disclosed, for example, in Zaborsky "*Immobilized Enzymes*" CRC Press, 1973, Table IV on pages 28-46.

Prior to equilibration and chromatography, the chromatography media (the support and adsorbent affixed to the support) may be pre-equilibrated in a chosen solution, e.g. a salt and/or buffer solution. Pre-equilibration serves the function of displacing a solution used for regenerating and/or storing the chromatography medium. One of skill in the art will realize that the composition of the pre-equilibration solution depends on the composition of the storage solution and the solution to be used for the subsequent chromatography. Thus, appropriate pre-equilibration solutions may include the same buffer or salt used for performing the chromatography, optionally, at a higher concentration than is used to perform chromatography. Buffers and salts that can be used for chromatography are discussed below. For example, when the solution used to perform chromatography comprises sodium phosphate at a given concentration, pre-equilibration may take place in a in a solution comprising sodium phosphate at a higher concentration. As an illustration of this, if the solution used to perform chromatography comprises sodium phosphate at between about 0.5 millimolar and about 50 millimolar, pre-equilibration may occur in a solution comprising sodium phosphate at concentrations between about 0.2 molar and about 0.5 molar, more preferably in concentrations of sodium phosphate between about 0.3 molar and about 0.4 molar, inclusive.

Before the sample is applied to the column, the column can be equilibrated in the buffer or salt that will be used to chromatograph the protein. As discussed below, chromatography (and loading of the protein to be purified) can occur in a variety of buffers or salts including sodium, potassium, ammonium, magnesium, calcium, chloride, fluoride, acetate, phosphate, and/or citrate salts and/or Tris buffer. Citrate buffers and salts are preferred by those skilled in the art for their ease of disposal. Such buffers or salts can have a pH of at least about 5.5. In some embodiments, equilibration may take place in a solution comprising a Tris or a sodium phosphate buffer. Optionally, the sodium phosphate buffer is at a concentration between about 0.5 millimolar and about 50 millimolar, more preferably at a concentration between about 15 millimolar and 35 millimolar. Preferably, equilibration takes place at a pH of at least about 5.5. Equilibration may take place at pHs between about 6.0 and about 8.6, preferably at pHs between about 6.5 and 7.5. Most preferably, the solution comprises a sodium phosphate buffer at a concentration of about 25 millimolar and at a pH of about 6.8.

Suitable buffers include, but are not limited to phosphate buffers, Tris buffers, acetate buffers, and/or citrate buffers. Acceptable salts may include, but are not limited to sodium chloride, ammonium chloride, potassium chloride, sodium acetate, ammonium acetate, sodium sulfate, ammonium sulfate, ammonium thiocyanate, sodium citrate, sodium phosphate, and potassium, magnesium, and calcium salts thereof, and combinations of these salts. In other embodiments, the salts include sodium citrate and sodium chloride. Acceptable ranges of salt concentrations used for chromatographic systems are typically in the range of from 0 to about 2M sodium citrate, 0 to about 4M sodium chloride, 0 to about 3M ammonium sulfate, 0 to about 1M sodium sulfate and 0 to about 2M sodium phosphate. The ranges of salt concentration may include 0 to about 1M sodium citrate, 0 to about 2M sodium chloride, 0 to about 1.5M ammonium sulfate, 0 to about 1M sodium sulfate and 0 to about 1.5M sodium phosphate. Other buffers and salts can also be used. After loading, the adsorbent can be washed with more of the same solution to cause the target protein (unbound to the adsorbent) to flow through the adsorbent. The protein is then collected in the flow-through fraction. Conditions for binding contaminants, while the target protein does not bind, can be easily optimized by those skilled in the art. The salt concentrations discussed herein are exemplary, and other salts and salt concentrations can be used by varying flow rates, temperatures, and elution times as is known in the art.

Conditions under which columns are used vary with the specific columns as is known in the art. For most proteins of interest, the pH range may be between about 6.0 and about 8.6, or alternatively between about 6.5 and about 7.5. However, certain proteins are known to be resistant to pH extremes, and a broader range may be possible. Typical conditions include a pH range of 5-7 and a sodium citrate concentration range of 0 to about 0.8M (e.g. 0.5M sodium citrate, pH 6.0).

One skilled in the art will be guided by the knowledge in the art in determining which buffer or salt is appropriate for the particular protein being purified. Moreover, a skilled artisan can easily determine the optimal concentration of the selected buffer or salt to use by, for example, establishing particular buffer or salt conditions under which contaminants bind to a column while the protein of interest flows through in the flow-through fraction. Fractions of the effluent of the column can be collected and analyzed to determine the concentration of buffer or salt at which the target protein and the contaminants elute. Suitable analyses include, for example, a measurement of electrical conductance with a conductivity meter (to determine the salt concentration in the sample) plus gel electrophoresis or ELISA assay (to determine the identity of the proteins in the sample). Optionally, the column can be washed with more of the same solution in which the protein sample was loaded, and this wash solution can also be collected and combined with the flow-through liquid.

Subsequent to collection of the flow through and, optionally, the wash, which comprises the protein being purified, proteins that may remain bound to the column may be released by stripping the chromatography medium using a solution comprising the buffer or salt used for chromatography, but at a lower ionic strength to release the contaminant proteins. Then, the column may be regenerated using a solution that will have the effect of releasing most or all proteins from the chromatography medium and reducing or eliminating any microbial contamination that may be present in the chromatography medium. In one embodiment, such a solution may comprise sodium hydroxide. Other reagents can also be used. Subsequently, the column may be rinsed and stored in a solution that can discourage microbial growth. Such a solution may comprise sodium hydroxide, but other reagents can also be appropriate.

Protein concentration of a sample at any stage of purification can be determined by any suitable method. Such methods are well known in the art and include: 1) colorimetric methods such as the Lowry assay, the Bradford assay, the Smith assay, and the colloidal gold assay; 2) methods utilizing the UV absorption properties of proteins; and 3) visual estimation based on stained protein bands on gels relying on comparison with protein standards of known quantity on the same gel. See e.g. Stoschek (1990), *Quantitation of Protein*, in Guide to Protein Purification, *Methods in Enzymol.* 182: 50-68.

The target protein, as well as contaminating proteins that may be present in a sample, can be monitored by any appropriate means. Preferably, the technique should be sensitive enough to detect contaminants in the range between about 2 parts per million (ppm) (calculated as nanograms per milligram of the protein being purified) and 500 ppm. For example, enzyme-linked immunosorbent assay (ELISA), a method well known in the art, may be used to detect contamination of the protein by the second protein. See e.g. Reen (1994), *Enzyme-Linked Immunosorbent Assay (ELISA)*, in Basic Protein and Peptide Protocols, Methods Mol. Biol. 32: 461-466, which is incorporated herein by reference in its entirety. In one aspect, contamination of the protein by such other proteins can be reduced after the methods described herein, preferably by at least about two-fold, more preferably by at least about three-fold, more preferably by at least about five-fold, more preferably by at least about ten-fold, more preferably by at least about twenty-fold, more preferably by at least about thirty-fold, more preferably by at least about forty-fold, more preferably by at least about fifty-fold, more preferably by at least about sixty-fold, more preferably by at least about seventy-fold, more preferably by at least about 80-fold, more preferably by at least about 90-fold, and most preferably by at least about 100-fold.

In another aspect, contamination of the protein by such other proteins after the methods described herein is not more than about 10,000 ppm, preferably not more than about 2500 ppm, more preferably not more than about 400 ppm, more preferably not more than about 360 ppm, more preferably not more than about 320 ppm, more preferably not more than about 280 ppm, more preferably not more than about 240 ppm, more preferably not more than about 200 ppm, more preferably not more than about 160 ppm, more preferably not more than about 140 ppm, more preferably not more than about 120 ppm, more preferably not more than about 100 ppm, more preferably not more than about 80 ppm, more preferably not more than about 60 ppm, more preferably not more than about 40 ppm, more preferably not more than about 30 ppm, more preferably not more than about 20 ppm, more preferably not more than about 10 ppm, and most preferably not more than about 5 ppm. Such contamination can range from undetectable levels to about 10 ppm or from about 10 ppm to about 10,000 ppm. If a protein is being purified for pharmacological use, one of skill in the art will realize that the preferred level of the second protein can depend on the weekly dose of the protein to be administered per patient, with the aim that the patient will not receive more than a certain amount of a contaminating protein per week. Thus, if the required weekly dose of the protein is decreased, the level of contamination by a second protein may possibly increase.

The amount of DNA that may be present in a sample of the protein being purified can be determined by any suitable method. For example, one can use an assay utilizing polymerase chain reaction. Optionally, the technique can detect DNA contamination at levels of 10 picograms per milligram of protein and greater. DNA levels can be reduced by HIC, optionally by about two-fold, preferably by about five-fold, more preferably by about ten-fold, more preferably by about fifteen-fold, most preferably by about 20-fold. Optionally, levels of DNA after hydroxyapatite chromatography are less than about 20 picograms per milligram of protein, preferably less than 15 picograms per milligram of protein, more preferably less than 10 picograms per milligram of protein, most preferably less than 5 picograms per milligram of protein.

Protein A-Based Chromatography

In one embodiment, the harvest media containing the antibody preparations may be purified by Protein A chromatography. Staphylococcal Protein A (SpA) is a 42 kDa protein composed of five nearly homologous domains named as E, D, A, B and C in order from the N-terminus (Sjodhal *Eur J Biochem* 78: 471-490 (1977); Uhlen et al. *J. Biol. Chem.* 259: 1695-1702 (1984)). These domains contain approximately 58 residues, each sharing about 65%-90% amino acid sequence identity. Binding studies between Protein A and antibodies have shown that while all five domains of SpA (E, D, A, B and C) bind to an IgG via its Fc region, domains D and E exhibit significant Fab binding (Ljungberg et al. *Mol. Immunol.* 30(14):1279-1285 (1993); Roben et al. *J. Immunol.* 154:6437-6445 (1995); Starovasnik et al. *Protein Sci* 8:1423-1431 (1999). The Z-domain, a functional analog and energy-minimized version of the B domain (Nilsson et al. *Protein Eng* 1:107-113 (1987)) was shown to have negligible binding to the antibody variable domain region (Cedergren et al. *Protein Eng* 6(4):441-448 (1993); Ljungberg et al. (1993) supra; Starovasnik et al. (1999) supra).

Until recently, commercially available Protein A stationary phases employed SpA (isolated from *Staphylococcus aureus* or expressed recombinantly) as their immobilized ligand. Using these columns, it has not been possible to use alkaline conditions for column regeneration and sanitation as is typically done with other modes of chromatography using non-proteinaceous ligands (Ghose et al. *Biotechnology and Bioengineering* Vol. 92 (6) (2005)). A new resin (Mab-SELECT™ SuRe) has been developed to withstand stronger alkaline conditions (Ghose et al. (2005) supra). Using protein engineering techniques, a number of asparagine residues were replaced in the Z-domain of protein A and a new ligand was created as a tetramer of four identically modified Z-domains (Ghose et al. (2005) supra).

Accordingly, purification methods can be carried out using commercially available Protein A columns according to manufacturers' specification. As described in the appended examples, MabSELECT™ columns or MabSELECT™ SuRe columns (GE Healthcare Products) can be used. MabSELECT™ is a commercially available resin containing recombinant SpA as its immobilized ligand. It captures antibody molecules from large media by packed bed chromatography. The recombinant Protein A ligand of MabSELECT™ is engineered to favor an orientation of the Protein A ligand that enhances binding capacity for IgG. The specificity of Protein A ligand to the binding region of IgG is similar to that of native Protein A. MabSELECT™ SuRe columns have a similar highly cross-linked agarose matrix used for MabSELECT™, the ligand used is a tetramer of four identically modified Z-domains (GE Healthcare Products). Other commercially available sources of Protein A column include, but are not limited to, PROSEP-ATM (Millipore, U.K.), which consists of Protein A covalently coupled to controlled pore glass, can be usefully employed. Other useful Protein A formulations include Protein A Sepharose FAST FLOW™ (Amersham Biosciences, Piscataway, N.J.), and TOYOPEARL™ 650M Protein A (Toso-Haas Co., Philadelphia, Pa.).

Hydroxyapatite Resins

Various hydroxyapatite chromatographic resins are available commercially, and any available form of the material can be used in the practice of this invention. A detailed description of the conditions suitable for hydroxyapatite chromatography is provided in WO 05/044856, the contents of which are incorporated by reference herein in its entirety.

In one embodiment of the invention, the hydroxyapatite is in a crystalline form. Hydroxyapatites for use in this invention may be those that are agglomerated to form particles and sintered at high temperatures into a stable porous ceramic mass. The particle size of the hydroxyapatite may vary widely, but a typical particle size ranges from 1 µm to 1,000 µm in diameter, and may be from 10 µm to 100 µm. In one embodiment of the invention, the particle size is 20 µm. In another embodiment of the invention, the particle size is 40 µm. In yet another embodiment of the invention, the particle size is 80 µm.

A number of chromatographic supports may be employed in the preparation of cHA columns, the most extensively used are Type I and Type I hydroxyapatite. Type I has a high protein binding capacity and better capacity for acidic proteins. Type II, however, has a lower protein binding capacity, but: has better resolution of nucleic acids and certain proteins. The Type II material also has a very low affinity for albumin and is especially suitable for the purification of many species and classes of immunoglobulins. The choice of a particular hydroxyapatite type can be determined by the skilled artisan.

This invention may be used with a hydroxyapatite resin that is loose, packed in a column, or in a continuous annual chromatograph. In one embodiment of the invention, ceramic hydroxyapatite resin is packed in a column. The choice of column dimensions can be determined by the skilled artisan. In one embodiment of the invention, a column diameter of at least 0.5 cm with a bed height of about 20 cm may be used for small scale purification.

In an additional embodiment of the invention, a column diameter of from about cm to about 60 cm may be used. In yet another embodiment of the invention, a column diameter of from 60 cm to 85 cm may be used. In certain embodiments of the invention, a slurry of ceramic hydroxyapatite resin in 200 mM $Na_2HPO4$ solution at pH 9.0 may be used to pack the column at a constant flow rate of about 4 cm/min or with gravity.

Buffer Compositions and Loading Conditions for Hydoxyapatite Resins

Before contacting the hydroxyapatite resin with the antibody preparation, it may be necessary to adjust parameters such as pH, ionic strength, and temperature and in some instances the addition of substances of different kinds. Thus, it is an optional step to perform an equilibration of the hydroxyapatite matrix by washing it with a solution (e.g., a buffer for adjusting pH, ionic strength, etc., or for the introduction of a detergent) bringing the necessary characteristics for purification of the antibody preparation.

In combination binding/flow-through mode hydroxyapatite chromatography, the hydroxyapatite matrix is equilibrated and washed with a solution, thereby bringing the necessary characteristics for purification of the antibody preparation. In one embodiment of the invention, the matrix may be equilibrated using a solution containing from 0.01 to 2.0 M NaCl at slightly basic to slightly acidic pH. For example, the equilibration buffer may contain 1 to 20 mM sodium phosphate, in another embodiment it may contain 1 to 10 mM sodium phosphate, in another embodiment it may contain 2 to 5 mM sodium phosphate, in another embodiment it may contain 2 mM sodium phosphate, and in another embodiment may contain 5 mM sodium phosphate. The equilibration buffer may contain 0.01 to 2.0 M NaCl, in one embodiment, 0.025 to 0.5 M NaCl, in another embodiment, 0.05 M NaCl, and in another, 0.1 M NaCl. The pH of the load buffer may range from 6.2 to 8.0. In one embodiment, the pH may be from 6.6 to 7.7, and in another embodiment the pH may be 7.3. The equilibration buffer may contain 0 to 200 mM arginine, in another embodiment it may contain 120 mM arginine, and in another embodiment it may contain 100 mM arginine. The equilibration buffer may contain 0 to 200 mM HEPES, in another embodiment it may contain 20 mM HEPES, and in another embodiment it may contain 100 mM HEPES.

The SDAB molecule preparation may also be buffer exchanged into an appropriate buffer or load buffer in preparation for flow-through mode hydroxyapatite chromatography. In one embodiment of the invention, the antibody preparation may be buffer exchanged into a load buffer containing 0.2 to 2.5 M NaCl at slightly acidic to slightly basic pH. For example, the load buffer may contain 1 to 20 mM sodium phosphate, in another embodiment it may contain 2 to 8 mM sodium phosphate, in another embodiment it may contain 3 to 7 mM sodium phosphate, and in another embodiment may contain 5 mM sodium phosphate. The load buffer may contain 0.2 to 2.5 M NaCl in one embodiment, 0.2 to 1.5 M NaCl, in another embodiment, 0.3 to 1.0 M NaCl, and in another embodiment, 350 mM NaCl. The pH of the load buffer may range from 6.4 to 7.6. In one embodiment, the pH may be from 6.5 to 7.0, and in another embodiment the pH may be 6.8.

The contacting of an SDAB molecule preparation to the hydroxyapatite resin in either binding mode, flow-through mode, or combinations thereof may be performed in a packed bed column, a fluidized/expanded bed column containing the solid phase matrix, and/or in a simple batch operation where the solid phase matrix is mixed with the solution for a certain time.

After contacting the hydroxyapatite resin with the antibody preparation there is optionally performed a washing procedure. However, in some cases where very high purity of the immunoglobulin is not critical or: additional flow-through antibody is not required, the washing procedure may be omitted, saving a process-step as well as washing solution. The washing buffers employed will depend on the nature of the hydroxyapatite resin, the mode of hydroxyapatite chromatography being employed, and therefore can be determined by one of ordinary skill in the art. In flow-through mode and combination binding/flow-through mode, the purified antibody flow-through obtained after an optional wash of the column may be pooled with other purified antibody fractions.

In binding mode, the SDAB molecule may be eluted from the column after an optional washing procedure. For elution of the antibody from the column, this invention uses a high ionic strength phosphate buffer containing about 0.2 to 2.5 M NaCl at slightly acidic to slightly basic pH. For example, the elusion buffer may contain 1 to 20 mM sodium phosphate, in another embodiment it may contain 2 to 8 mM sodium phosphate, in another embodiment it may contain 2 to 6 mM sodium phosphate, in another embodiment may contain 3 mM sodium phosphate, and in another embodiment may contain 5 mM sodium phosphate. The elusion buffer may contain 0.2 to 2.5 M NaCl, in one embodiment, 0.2 to 1.5 M NaCl, in another embodiment, 0.3 to 1.1 M NaCl, in another embodiment, 1.0 M NaCl, and in another embodiment, 0.35 M NaCl. The pH of the elusion buffer may range from 6.4 to 7.6. In one embodiment, the pH may be from 6.5 to 7.3, in another embodiment the pH may be 7.2, and in another embodiment the pH may be 6.8. The elusion buffer may be altered for elusion of the antibody from the column in a continuous or stepwise gradient.

In both the binding mode, flow-through mode, and combinations thereof, a solid phase matrix may optionally be cleaned, i.e. stripped and regenerated, after elusion or flow through of the antibody. This procedure is typically performed regularly to minimize the building up of impurities on the surface of the solid phase and/or to sterilize the matrix to avoid contamination of the product with microorganisms.

Buffer components may be adjusted according to the knowledge of the person of ordinary skill in the art.

Additional Optional Steps

Although it has been discovered that hydroxyapatite chromatography can be used alone to separate monomeric IgG from aggregates, as mentioned above, the purification method of the invention can be used in combination with other protein purification techniques. In one embodiment of the invention, one or more steps preceding the hydroxyapatite step may be desirable to reduce the load challenge of the contaminants or impurities. In another embodiment of the invention, one or more purification steps following the hydroxyapatite step may be desirable to remove additional contaminants or impurities.

The cHA purification procedure described may optionally be i combined with other purification steps, including but not limited to, Protein A chromatography, affinity chromatography, hydrophobic interaction chromatography, immobilized metal affinity chromatography, size exclusion chromatography, diafiltration, ultrafiltration, viral removal filtration, and/or ion exchange chromatography.

In one embodiment, prior to the cHA purification step, the harvest media may optionally be initially purified by a Protein A chromatography step. For example, PROSEP-A™ (Millipore, U.K.), which consists of Protein A covalently coupled to controlled pore glass, can be usefully employed. Other useful Protein A formulations include Protein A Sepharose FAST FLOW™ (Amersham Biosciences, Piscataway, N.J.), TOYOPEARL™ 650M Protein A (TosoHaas Co., Philadelphia, Pa.), and MABSELECT™ columns (Amersham Biosciences, Piscataway, N.J.).

As an optional step prior to the cHA purification, ion exchange chromatography may be employed. In this regard various anionic or cationic substituents may be attached to matrices in order to form anionic or cationic supports for chromatography. Anionic exchange substituents include diethylaminoethyl (DEAE), trimethylandinoethyl acrylamide (TMAE), quaternary aminoethyl (QAE) and quaternary amine (Q) groups. Cationic exchange substituents include carboxymethyl (CM), sulfoethyl (SE), sulfopropyl (SP), phosphate (P) and sulfonate (S). Cellulosic ion exchange resins such as DE23, DE32, DE52, CM-23, CM-32 and CM-52 are available from Whatman Ltd. Maidstone, Kent, U.K. Sephadex-based and cross-linked; ion exchangers are also known. For example, DEAE-, QAE-, CM-, and SP Sephadex, and DEAE-, Q-, CM- and S-Sepharose, and Sepharose are all available from Amersham Biosciences, Piscataway, N.J. Further, both DEAE and CM derivitized ethylene glycol-methacrylate copolymer such as TOYOPEARL™ DEAE-650S or M and TOYOPEARL™ CM-650S or M are available from Toso Haas Co., Philadelphia, Pa.

In one embodiment of the invention, ion exchange chromatography may be used in binding mode or flow-through mode.

In certain embodiments, the Protein A chromatography step is conducted first, the anion exchange step is conducted second, and the cHA step is conducted third.

Removal of Additional Impurities

In addition to HMWA removal, cHA chromatography has been shown useful in removing other impurities from antibody preparations. Other impurities that may be removed by the cHA chromatography methods of the invention include, but are not limited to, DNA, host cell protein, adventitious viruses, and Protein A contaminants from prior purification steps.

In one embodiment of the invention, the invention is able to remove Protein A from the antibody preparation. In certain embodiments of this invention, the amount of Protein A present in the final preparation can be reduced significantly, such as from 300 ppm to less than 1 ppm.

Administration and Method of Treatment

Formulations containing the SDAB molecules purified by the methods disclosed herein can be administered to a subject (e.g., a human subject) alone or combination with a second agent, e.g., a second therapeutically or pharmacologically active agent, to treat or prevent (e.g., reduce or ameliorate one or more symptoms associated with) a TNFα associated disorder, e.g., inflammatory or autoimmune disorders. The term "treating" refers to administering a therapy in an amount, manner, and/or mode effective to improve a condition, symptom, or parameter associated with a disorder or to prevent progression of a disorder, to either a statistically significant degree or to a degree detectable to one skilled in the art. An effective amount, manner, or mode can vary depending on the subject and may be tailored to the subject.

Non-limiting examples of immune disorders that can be treated include, but are not limited to, autoimmune disorders, e.g., arthritis (including rheumatoid arthritis, juvenile rheumatoid arthritis, osteoarthritis, psoriatic arthritis, lupus-associated arthritis or ankylosing spondylitis), scleroderma, systemic lupus erythematosis, Sjogren's syndrome, vasculitis, multiple sclerosis, autoimmune thyroiditis, dermatitis (including atopic dermatitis and eczematous dermatitis), myasthenia gravis, inflammatory bowel disease (IBD), Crohn's disease, colitis, diabetes mellitus (type I); inflammatory conditions of, e.g., the skin (e.g., psoriasis); acute inflammatory conditions (e.g., endotoxemia, sepsis and septicaemia, toxic shock syndrome and infectious disease); transplant rejection and allergy. In one embodiment, the TNFα associated disorder is, an arthritic disorder, e.g., a disorder chosen from one or more of rheumatoid arthritis, juvenile rheumatoid arthritis (RA) (e.g., moderate to severe rheumatoid arthritis), osteoarthritis, psoriatic arthritis, or ankylosing spondylitis, polyarticular juvenile idiopathic arthritis (JIA); or psoriasis, ulcerative colitis, Crohn's disease, inflammatory bowel disease, and/or multiple sclerosis.

In certain embodiments, the formulations include a second therapeutic agent. For example, for TNF-nanobodies, the second agent may be an anti-TNF antibody or TNF binding fragment thereof, wherein the second TNF antibody has a different epitope specificity than the TNF-binding SDAB molecule of the formulation. Other non-limiting examples of agents that can be co-formulated with TNF-binding SDAB include, for example, a cytokine inhibitor, a growth factor inhibitor, an immunosuppressant, an anti-inflammatory agent, a metabolic inhibitor, an enzyme inhibitor, a cytotoxic agent, and a cytostatic agent. In one embodiment, the additional agent is a standard treatment for arthritis, including, but not limited to, non-steroidal anti-inflammatory agents (NSAIDs); corticosteroids, including prednisolone, prednisone, cortisone, and triamcinolone; and disease modifying anti-rheumatic drugs (DMARDs), such as methotrexate, hydroxychloroquine (Plaquenil) and sulfasalazine, leflunomide (Arava®), tumor necrosis factor inhibitors, including etanercept (Enbrel®), infliximab (Remicade®) (with or without methotrexate), and adalimumab (Humira®), anti-CD20 antibody (e.g., Rituxan®), soluble interleukin-1 receptor, such as anakinra (Kineret), gold, minocycline (Minocin®), penicillamine, and cytotoxic agents, including azathioprine, cyclophosphamide, and cyclosporine. Such combination therapies may advantageously utilize lower dosages of the administered therapeutic agents, thus avoiding possible toxicities or complications associated with the various monotherapies.

The formulations can be in the form of a liquid solution (e.g., injectable and infusible solutions). Such compositions can be administered by a parenteral mode (e.g., subcutaneous, intraperitoneal, or intramuscular injection), or by inhalation. The phrases "parenteral administration" and "administered parenterally" as used herein mean modes of administration other than enteral and topical administration, usually by injection, and include, subcutaneous or intramuscular administration, as well as intravenous, intracapsular, intraorbital, intracardiac, intradermal, intraperitoneal, transtracheal, subcuticular, subcapsular, subarachnoid, intraspinal, epidural and intrasternal injection and infusion. In one embodiment, the formulations described herein are administered subcutaneously.

Pharmaceutical formulations are sterile and stable under the conditions of manufacture and storage. A pharmaceutical composition can also be tested to insure it meets regulatory and industry standards for administration.

A pharmaceutical formulation can be formulated as a solution, microemulsion, dispersion, liposome, or other ordered structure suitable to high protein concentration. Sterile injectable solutions can be prepared by incorporating an agent described herein in the required amount in an appropriate solvent with one or a combination of ingredients enumerated above, as required, followed by filtered sterilization. Generally, dispersions are prepared by incorporating an agent described herein into a sterile vehicle that contains a basic dispersion medium and the required other ingredients from those enumerated above. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

EXAMPLES

The following examples are offered for illustrative purposes only.

Example 1: Description of the ATN-103 Coding Sequence

Figure 3:
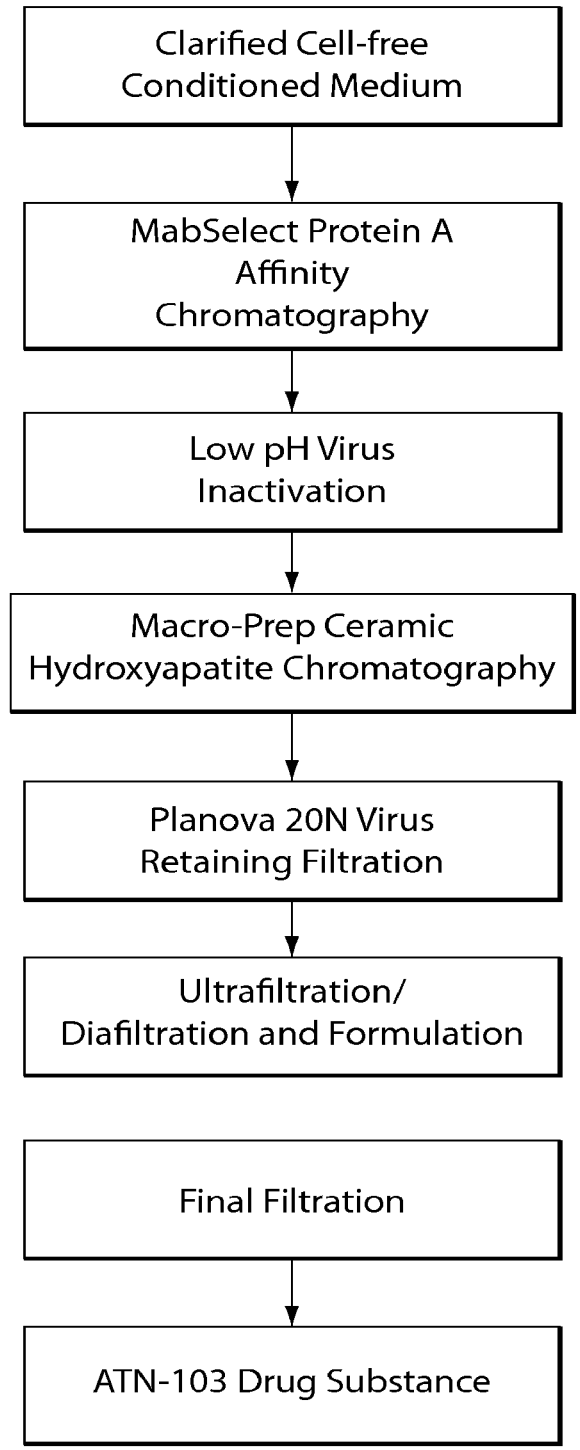
FIG. 3 depicts a flow diagram of the ATN-103 purification process.

ATN-103 is a trivalent nanobody molecule targeting TNFα and HSA. Nanobodies were isolated from a llama derived phage library by selection on TNFα or HAS as described in WO 06/122786. Nanobodies were tested for specific activity and TNF1 was chosen as the nanobody inhibitor of human TNFα and ALB1 the human anti-HSA nanobody for half-life extension. TNF1 and ALB1 were humanized by CDR grafting onto the closest human framework (DP51/DP53). During humanization of TNF1, 2 camelid residues were retained (P84 and R103) and this version designated TNF30. During humanization of ALB1, 7 camelid residues were retained (N16, N73, T76, P84, T93, 194 and 5103) and this version designated ALB8. Two TNF30 nanobodies were each linked by a 9 amino-acid Glycine-Serine linker ($Gly_4SerGly_3Ser$ (SEQ ID NO:9)) to a central ALB8 nanobody to give the trivalent molecule designated herein as "ATN-103." The amino acid sequence of ATN-103 is shown in FIG. 3 having the following configuration—TNF30-(Glycine-Serine linker)-ALB8-(Glycine-Serine linker)-TNF30. In FIG. 2, complementarity determining regions (CDR) are underlined (SEQ ID NOs:2-7). The predicted intramolecular disulfide bonds are illustrated by connections of the cysteine residues involved. The binding domains to TNF are shown in bold and the binding domain to HSA is shown in bold italics. The amino acid linkers connecting these binding domains are in italics. The signal peptide ($^{-19}$MGW . . . VHS$^{-1}$) is) also shown for the polypeptide chain.

Example 2: ATN-103 Purification Process

The ATN-103 purification process consists of two chromatographic steps and three membrane filtration steps (see FIG. 3). All steps are performed at room temperature unless indicated otherwise.

The principles, objectives, and descriptions of each purification step are provided below.

MabSelect Protein A Affinity Chromatography and Low pH Virus Inactivation

The primary objectives of the MabSelect™ Protein A chromatography step include product capture from clarified cell-free conditioned medium and separation of ATN-103 from process-derived impurities (e.g., host cell DNA and protein, medium components, and adventitious agents).

MabSelect Protein A is an affinity resin composed of a highly cross-linked agarose matrix that is covalently derivatized through a thioether linkage with recombinant Protein A produced from *Escherichia coli* (*E. coli*) fermentation.

The MabSelect Protein A column is equilibrated with Tris-buffered sodium chloride solution and loaded with clarified cell-free conditioned medium (CM). All buffers run at 300 cm/hr. The equilibration buffer contains 150 mM NaCl and 50 mM Tris at pH 7.5. ATN-103 binds to the MabSelect™ Protein A resin and impurities flow through the column. The loaded resin is washed with a Tris-buffered sodium chloride solution (150 mM NaCl and 50 mM Tris at pH 7.5) to further reduce the level of impurities, followed by a low concentration Tris buffer. The low concentration Tris washing buffer contains 10 mM NaCl and 10 mM Tris at pH 7.5. The bound product is eluted from the column with a low pH glycine buffer. The low pH glycine elution buffer contains 10 mM NaCl and 50 mM glycine at pH 3.0. The resin is regenerated and sanitized with a hydroxide solution and then stored in a solution containing 16% ethanol. Multiple cycles of the MabSelect Protein A step can be generated from one harvest.

The product pool is held at pH≤3.8 for 1.5±0.5 h at 18° C. to 24° C. The low pH inactivation following the MabSelect™ Protein A column has been designed to inactivate enveloped viruses. The elution pool is then neutralized with a concentrated HEPES buffer (2 mM HEPES at pH 9.0) and filtered using depth and 0.2 μm filtration.

Macro-Prep Ceramic Hydroxyapatite Chromatography

The primary objectives of the Macro-Prep™ ceramic hydroxyapatite (cHA) step are the removal of high molecular weight aggregates (HMWA), leached Protein A, and host cell-derived impurities, such as DNA and host cell proteins (HCPs).

Macro-Prep ceramic hydroxyapatite is an incompressible matrix composed of a hexagonally-crystalline lattice. Calcium, phosphate, and hydroxide molecules comprise the matrix, with a stoichiometry of $(Ca_5(PO_4)_3(OH))_2$. The cHA resin is a multi-mode matrix capable of promoting cation exchange, anion exchange, and metal coordination interactions. Elution of bound proteins is typically achieved with increases in salt or phosphate concentration.

The cHA column is first equilibrated with a buffer containing a high concentration of sodium chloride followed by a buffer containing a low concentration of sodium chloride. The load to the cHA column is the neutralized MabSelect™ Protein A pool. After loading, the column is washed with a low salt equilibration buffer and ATN-103 is recovered using a buffer containing higher salt concentration. After elution of ATN-103, HMW and other impurities are removed from the column at much higher salt and phosphate concentrations. The column is regenerated and then stored in a sodium hydroxide solution.

Planova 20N Virus Retaining Filtration

The Planova 20N virus retaining filtration (VRF) step provides a significant level of viral clearance for assurance of product safety by removal of particles that may represent potential adventitious viral contaminants.

The single-use Planova 20N VRF device is equilibrated cHA elution buffer and loaded with the Macro-Prep ceramic hydroxyapatite product pool. The product is collected in the permeate stream. After the load is processed, a buffer flush is used to recover additional product remaining in the system.

Ultrafiltration/Diafiltration and Formulation

An ultrafiltration/diafiltration step (10 kDa MW cut off) is used to concentrate and buffer exchange the VRF product into the formulation buffer.

After equilibration of the membrane module, the load solution is initially concentrated to a preset target volume and then diafiltered with 14 mM Histidine pH 5.8 buffer. Following further concentration to approximately 110 g/L, the pool is recovered from the system with a histidine buffer flush to achieve a final protein target concentration of approximately 90 g/L. A small volume (11.1% v/v) of concentrated stock solution (10 mM Histidine, 50% Sucrose and 0.1% Polysorbate 80) is added to the product pool. The final drug substance (DS) obtained is 80 g/L ATN-103 in 10 mM Histidine pH 6.0, 5% sucrose, 0.01% Polysorbate.

Final Filtration

The formulated drug substance is passed through a single-use 0.2 μm filter to remove any potential adventitious microbial contaminants and particulate material.

Example 3: Protein A Capture Comparison

The following Protein A based matrixes were evaluated for their capacities to capture ATN-103: MabSelect™ (GE Healthcare), MabSelect Xtra™ (GE Healthcare), ProSep® Va Ultra Plus (Millipore), and MabSelect SuRe™ (GE Healthcare). MabSelect™ uses Protein A ligand containing Z-domain and the resin backbone is more hydrophobic due to cross linking. MabSelect Xtra™ uses the same ligand as MabSelect with 30% increased density and has smaller beads and larger pore size. ProSep® Va Ultra Plus has glass based backbone and native Protein A ligand. It is designed for higher capacities at higher flow rates. MabSelect SuRe™ binds Fc containing molecules (ATN-103 does not have an Fc region) and its novel ligand allows for greater caustic stability.

When a Protein A peak pool, which had been purified by MabSelect™, was used as the loading material (pH=7.0, diluted to 1 g/L (expected condition media concentration)), ProSep® Va Ultra Plus showed the highest binding capacity (16 g/L r) and the binding capacity of MabSelect™ showed a 20% increase compared to previously demonstrated binding capacity.

The impact of flow rate on Dynamic Binding Capacity (DBC) was examined. For MabSelect™, the binding capacity was 7.4 g/L r at 600 cm/hr, compared to 8.0 g/L r at 60 cm/hr. Similar trend was observed when MabSelect Xtra™ and ProSep® Va Ultra Plus were tested. Thus, there was minimal impact of flow rate on DBC under the tested conditions.

The effect of modifier on Protein A binding capacity was also examined. The results showed that the addition of 0.5 M $Na_2SO_4$ could increase DBC by enhancing hydrophobic interactions. For example, the binding capacity for MabSelect™ (with CM) increased to 12.5 g/L r with the flow rate of 150 cm/hr. Additional bound material was subsequently eluted in $Na_2SO_4$ free solution. High amount of precipitation was detected in CM with $Na_2SO_4$. Similar results were observed when MabSelect Xtra™ (DBC=16 g/L r) and ProSep® Va Ultra Plus (DBC=17.5 g/L r) were tested.

To examine the effect of PEG on Protein A binding capacity, 6% PEG (4000 Da) was added into CM. Additional bound material was subsequently eluted in PEG free buffer. The results showed a slight increase in binding capacity and no precipitation was detected.

Example 4: ATN-103 MabSelect SuRe™ Evaluation

During the development of the MabSelect step MabSelect Sure™ was used in binding experiments to gain a better understanding of the Protein A binding mechanism to ATN-103. Unexpectedly, the ATN-103 bound to MabSelect Sure™ and required a solution with pH 4.5 to remove the bound product. MabSelect Sure is Protein A resin that was designed to bind only molecules containing an Fc region such as antibodies. ATN-103 does not contain an Fc region. Later in development it was determined that MabSelect Sure™ could bind up to 8 g/L resin of ATN-103 at 10% breakthrough of the initial concentration.

Example 5: ATN-103 Cation Exchange (CEX) Step Evaluation

A Cation Exchange (CEX) based capture step was evaluated in an effort to increase the capacity of the capture column in the ATN-103 purification process. By lowering the conductivity of the condition media (CM) between 12 and 9 mS/cm and titrating the pH to ≤4.3 a capacity of 40 g/L r were observed. ATN-103 binds very weakly to the CEX medium due to the low number of charge/mole at these pH levels. Because of this weak binding, ATN-103 can be eluted from the CEX resin in low conductivity solutions. The eluting conditions were generally ≤50 mM NaCl at pH 6.5 to 7.0. The CEX column could also be eluted using the downstream cHA equilibration buffer.

CEX Capacity Screen

Four cation exchangers, Capto™ S (GE Heathcare), Fractogel® SO3-(M) (EMD Chemicals), Toyopearl® Gigacap S-650M (Tosoh Bioscience) and Poros® HS 50 (Applied Biosystems), were tested for their binding capacities for ATN-103. 0.75 mL CM TS2 with 10 uL resin (target 75 g/L resin) was used in the screening. Columns were washed with buffer containing 50 mM sodium acetate at the same pH as the loading condition. Proteins were eluted with buffer containing 1M NaCl (pH 5.5). The bound mass was measured by spectrophotometry at A280. Columns were subsequently stripped with buffer containing 1M NaCl and Urea. Spectrophotometry measured at A280 showed that no significant mass was bound after stripping. Up to about 25 g/L r of binding capacity was observed for all resins studied. Capto™ S and Toyopearl® Gigacap S-650M showed relatively weaker binding, and Fractogel® SO3-(M) and Poros® HS 50 showed tighter binding. This study indicates that elution by pH with very low conductivity conditions is possible.

CEX Binding Capacity

CM were titrated to pH4.0 and diluted 3:1 with Rodi water (3 parts CM was added to 1 part Rodi) to 0.75 total dilution (8 mS/cm load). Binding capacities of Capto™ S, Toyopearl® Gigacap S-650M, Poros® HS 50 and Fractogel® SO3-(M) were initially measured for a target binding capacity of greater than 40 g/L using 2 mL column (0.5 cm×10 cm). The binding capacities of Capto™ S, Toyopearl® Gigacap S-650M and Fractogel® SO3-(M) were further determined at various conditions within a pH range from 4.0 to 4.3. For example, the binding capacity for Capto™ S was measured at pH 4.3, 9 mS/cm; pH 4.0, 11 mS/cm, pH 4.0, 9 mS/cm, and pH 4.1, 8 mS/cm, respectively. The binding capacity for Toyopearl® Gigacap S-650M was measured at pH 4.3, 9 mS/cm and pH 4.1, 8 mS/cm. The binding capacity for Fractogel® SO3-(M) was measured at pH 4.3, 12 mS/cm; pH 4.3, 9 mS/cm; pH 4.0, 12 mS/cm, pH 4.1, 9 mS/cm, and pH 4.0, 9 mS/cm, respectively. The results showed that Fractogel® SO3-(M) could be used without diluting CM with water. Without dilution Fractogel® SO3-(M) showed good binding capacity between pH 4.0 and 4.3 (DBC range: 25 to >40 g/L r). With 23% dilution, Fractogel® SO3-(M) showed excellent capacity between pH 4.0 and 4.3 (DBC range: 40 to >50 g/L r).

CEX Elution Approach

Gradient elutions were performed as described in the experiments for CEX binding capacity. Citrate buffer was used for pH elution. Capto™ S, Toyopearl® Gigacap S-650M, Fractogel® SO3-(M) and Poros® HS 50 were tested. Size exclusion chromatography (SEC) elution showed high purity of ATN-103 and low level of HMW and LMW species. The degree of purity is at least comparable to that of the Protein A eluted materials. HTS screen can be designed with the information obtained from the gradient elutions.

Example 6: High Concentration
Ultrafiltration/Diafiltration and Formulation

Example 6.1: High Concentration
Ultrafiltration/Diafiltration and Formulation

An ultrafiltration/diafiltration step (10 kDa MW cut off) is used to concentrate and buffer exchange the VRF product into the formulation buffer.

After equilibration of the membrane module, the load solution is initially concentrated to a preset target volume and then diafiltered with 28 mM Histidine pH 5.8 buffer. Following further concentration to approximately 200 g/L, the pool is recovered from the system with a histidine buffer flush to achieve a final protein target concentration of approximately 150 g/L. A small volume (17.6% v/v) of concentrated stock solution (20 mM Histidine, 50% Sucrose and 0.0667% Polysorbate 80) is added to the product pool 80. The final DS obtained is 80 g/L ATN-103 in 10 mM Histidine pH 6.0, 5% sucrose, 0.01% PS80. The final DS obtained is 125 g/L ATN-103 in 20 mM Histidine pH 6.0, 7.5% sucrose, 0.01% Polysorbate.

Example 6.2: High Concentration
Ultrafiltration/Diafiltration

An ultrafiltration/diafiltration step (10 kDa MW cut off) was used to concentrate and buffer exchange the VRF product into the formulation buffer.

After equilibration of the membrane module, the load solution was initially concentrated to approximately 40 g/L and then diafiltered with 30 mM Histidine, pH 5.8, 8.5% Sucrose buffer. Following further concentration to approximately 300 g/L, the pool was recovered from the system with diafiltration buffer to achieve a final protein target concentration of approximately 175 g/L.

Example 6.3: High Concentration
Ultrafiltration/Diafiltration and Formulation

An ultrafiltration/diafiltration step (10 kDa MW cut off) was used to concentrate and buffer exchange the VRF product into the formulation buffer.

After equilibration of the membrane module, the load solution was initially concentrated to approximately 40 g/L and then diafiltered with 30 mM Histidine pH 5.8 buffer. Following further concentration to approximately 320 g/L, the pool was recovered from the system with diafiltration buffer to achieve a final protein target concentration of approximately 210 g/L.

If the DS target was >=200 g/L, a combination of Example 6.2 and Example 6.3 would be performed as follows: An ultrafiltration/diafiltration step (10 kDa MW cut off) could be used to concentrate and buffer exchange the VRF product into the formulation buffer. After equilibration of the membrane module, the load solution could be initially concentrated to 40 g/L and then diafiltered with a histidine sucrose buffer. Following further concentration to approximately 320 g/L, the pool would be recovered from the system with diafiltration buffer to achieve a final protein target concentration of approximately >=200 g/L where the sucrose is already present. Then the formulation spike would be 1.01% v/v so the UF pool won't get significantly diluted and the final DS would be >=200 g/L.

EQUIVALENTS

All references cited herein are incorporated herein by reference in their entirety and for all purposes to the same extent as if each individual publication or patent or patent application was specifically and individually indicated to be incorporated by reference in its entirety for all purposes.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

We claim:

1. A method of separating or purifying a single domain antigen binding (SDAB) molecule that comprises one or more nanobody molecules from a mixture containing the SDAB molecule and one or more contaminants, comprising:
   (a) contacting the mixture with a support that comprises tetramer of a modified B-domain (SEQ ID NO: 12) of Protein A under conditions that allow the SDAB molecule to bind or absorb to the support;
   (b) removing one or more of the contaminants; and
   (c) selectively eluting the SDAB molecule from the support,
   wherein said SDAB molecule does not have a complementary antibody variable domain or an immunoglobulin Fc region, and
   wherein the step of removing one or more of the contaminants comprises washing the bound support under conditions where the SDAB molecule remains bound to the support.

2. The method of claim 1, wherein the step of removing one or more of the contaminants comprises washing the bound support with at least one Protein A washing buffer, wherein said Protein A washing buffer comprises about 100 to about 175 mM NaCl and about 40 to about 60 mM Tris at pH ranging from about 7 to 7.5.

3. The method of claim 1, wherein the step of selectively eluting the SDAB molecule from the support comprises eluting the adsorbed SDAB molecule with at least one Protein A elution buffer, wherein said Protein A elution buffer comprises about 5 to about 50 mM NaCl and about 5 mM to about 100 mM glycine at pH 4.0 or less.

4. The method of claim 1, further comprising one or more of: hydroxyapatite chromatography, cation exchange chromatography, affinity chromatography, size exclusion chromatography, hydrophobic interaction chromatography, metal affinity chromatography, diafiltration, ultrafiltration, viral inactivation or viral removal filtration.

5. The method of claim 1, wherein the SDAB molecule is a single chain polypeptide, comprising at least one immunoglobulin variable domain.

6. The method of claim 1, wherein the SDAB molecule:
   (a) comprises at least one immunoglobulin variable domain from an antibody naturally devoid of light chains,
   (b) is a monovalent, bivalent, or trivalent molecule; or
   (c) is a monospecific, bispecific, or trispecific molecule.

7. The method of claim 6, wherein the antibody naturally devoid of light chains in (a) is a camelid antibody.

8. The method of claim 1, wherein the SDAB molecule comprises one or more nanobody molecules that are recombinant, CDR-grafted, humanized, camelized, deimmunized, and/or in vitro selected by phage display.

9. The method of claim 1, wherein the SDAB molecule is a trivalent, bispecific molecule.

10. The method of claim 1, wherein:
    (a) the SDAB molecule comprises the amino acid sequence of SEQ ID NO:1;
    (b) the SDAB molecule comprises at least one nanobody molecule that binds to tumor necrosis factor a (TNFα) and comprises three CDRs having the amino sequence: SEQ ID NO: 2 (DYWMY (CDR1)), SEQ ID NO: 3 (EINTNGLITKYPDSVKG (CDR2)) and SEQ ID NO: 4 (SPSGFN (CDR3)), or having a CDR that differs by fewer than 2 conservative amino acid substitutions from one of said CDRs; or
    (c) the SDAB molecule comprises at least one nanobody molecule that binds to TNFα and comprises a variable region having the amino acid sequence from about amino acids 1 to 115 of SEQ ID NO: 1.

11. The method of claim 1, wherein the SDAB molecule comprises two or more nanobody molecules, wherein at least two of the two or more of nanobody molecules are fused with a linking group comprising the amino acid sequence of SEQ ID NO: 9 ((Gly)$_4$-Ser(Gly)$_3$-Ser).

12. The method of claim 1, further comprising concentrating the eluted SDAB molecule to a preselected target volume.

13. The method of claim 12, wherein the concentrating step is carried out by performing an ultrafiltration/diafiltration step in the presence of a histidine buffer or a Tris buffer.

14. A method of separating or purifying a single domain antigen binding (SDAB) molecule that comprises one or more nanobody molecules from a mixture containing the SDAB molecule and one or more contaminants, comprising:
    (a) contacting the mixture with a support that comprises a tetramer of a modified B-domain (SEQ ID NO: 12) of Protein A under conditions that allow the SDAB molecule to bind or absorb to the support;
    (b) removing one or more of the contaminants, wherein the step of removing one or more of the contaminants comprises washing the bound support under conditions where the SDAB molecule remains bound to the support;
    (c) selectively eluting the SDAB molecule from the support, thereby obtaining an eluted SDAB molecule preparation; and
    (d)(i) contacting the eluted SDAB molecule preparation with a hydroxyapatite resin;
    and selectively eluting the SDAB molecule from the hydroxyapatite resin, or (d)(ii) pre-treating the eluted SDAB molecule preparation with an equilibration buffer; and allowing the pre-treated mixture to flow through a hydroxyapatite resin;
    wherein said SDAB molecule does not have a complementary antibody variable domain or an immunoglobulin Fc region.

15. A method or process of providing a recombinant single domain antigen binding (SDAB) molecule that includes one or more nanobody molecules, comprising:
    (a) providing a mammalian host cell comprising a nucleic acid that encodes the recombinant SDAB molecule;
    (b) maintaining the host cell under conditions in which the recombinant SDAB molecule is expressed;

(c) obtaining a mixture of the recombinant SDAB molecule and one or more contaminants;
(d) purifying or separating the recombinant SDAB molecule from said mixture using a chromatography support which comprises a tetramer of a modified B-domain (SEQ ID NO: 12) of Protein A, wherein said purifying or separating step comprises contacting the mixture with the support under conditions that allow the SDAB molecule to bind or absorb to the support;
(e) removing one or more of the contaminants, wherein the step of removing one or more of the contaminants comprises washing the bound support under conditions wherein the SDAB molecule remains bound to the support; and
(f) selectively eluting the SDAB molecule from the support, thereby obtaining an eluted SDAB molecule preparation,
wherein said SDAB molecule does not have a complementary antibody variable domain or an immunoglobulin Fc region.

16. The method of claim 15, further comprising subjecting the eluted SDAB molecule preparation to one or more of hydroxyapatite chromatography, affinity chromatography, size exclusion chromatography, hydrophobic interaction chromatography, metal affinity chromatography, diafiltration, ultrafiltration, or viral removal filtration.

17. The method of claim 10, wherein the SDAB molecule of (b) further comprises at least one nanobody molecule that binds to human serum albumin (HSA) and comprises three CDRs having the amino acid sequence: SFGMS (CDR1; SEQ ID NO: 5), SISGSGSDTLYADSVKG (CDR2; SEQ ID NO: 6) and/or GGSLSR (CDR3; SEQ ID NO: 7), or having a CDR that differs by fewer than 2 conservative amino acid substitutions from one of said CDRs.

18. The method of claim 17, wherein said at least one nanobody molecule that binds to HSA comprises a variable region having the amino acid sequence from about amino acids 125 to 239 of SEQ ID NO: 1.

* * * * *

UNITED STATES PATENT AND TRADEMARK OFFICE
CERTIFICATE OF CORRECTION

| | |
|---|---|
| PATENT NO. | : 11,370,835 B2 |
| APPLICATION NO. | : 16/142198 |
| DATED | : June 28, 2022 |
| INVENTOR(S) | : Paul R. Brown et al. |

It is certified that error appears in the above-identified patent and that said Letters Patent is hereby corrected as shown below:

In the Claims

Column 49, Line 51, Claim 6, should read as follows:
6. The method of claim 1, wherein the SDAB molecule:
    (a) comprises at least one immunoglobulin variable domain from an antibody naturally devoid of light chains;
    (b) is a monovalent, bivalent, or trivalent molecule; or
    (c) is a monospecific, bispecific, or trispecific molecule.

Columns 49-50, Lines 65-22, Claim 10, should read as follows:
10. The method of claim 1, wherein:
    (a) the SDAB molecule comprises the amino acid sequence of SEQ ID NO: 1;
    (b) the SDAB molecule comprises at least one nanobody molecule that binds to tumor necrosis factor α (TNFα) and comprises three CDRs having the amino acid sequence: SEQ ID NO: 2 (DYWMY (CDR1)), SEQ ID NO: 3 (EINTNGLITKYPDSVKG (CDR2)) and SEQ ID NO: 4 (SPSGFN (CDR3)), or having a CDR that differs by fewer than 2 conservative amino acid substitutions from one of said CDRs; or
    (c) the SDAB molecule comprises at least one nanobody molecule that binds to TNFα and comprises a variable region having the amino acid sequence from about amino acids 1 to 115 of SEQ ID NO: 1.

Signed and Sealed this
First Day of November, 2022

Katherine Kelly Vidal
*Director of the United States Patent and Trademark Office*